(12) United States Patent
Moser et al.

(10) Patent No.: US 7,761,238 B2
(45) Date of Patent: Jul. 20, 2010

(54) METHOD AND APPARATUS FOR DISCOVERING PATTERNS IN BINARY OR CATEGORICAL DATA

(75) Inventors: Allan Robert Moser, 815 Westdale Ave., Swarthmore, PA (US) 19081-1905; Wade Thomas Rogers, West Chester, PA (US); Dennis John Underwood, Jamaica Plain, MA (US)

(73) Assignee: Allan Robert Moser, Swarthmore, PA (US)

( * ) Notice: Subject to any disclaimer, the term of this patent is extended or adjusted under 35 U.S.C. 154(b) by 591 days.

(21) Appl. No.: 10/956,671

(22) Filed: Oct. 1, 2004

(65) Prior Publication Data

US 2005/0143928 A1 Jun. 30, 2005

Related U.S. Application Data

(60) Provisional application No. 60/508,825, filed on Oct. 3, 2003.

(51) Int. Cl.
*G06F 19/00* (2006.01)
*G06F 7/38* (2006.01)

(52) U.S. Cl. .......................... 702/19; 702/20
(58) Field of Classification Search ........................ None
See application file for complete search history.

(56) References Cited

U.S. PATENT DOCUMENTS 5,701,256 A * 12/1997 Marr et al. .................... 702/20
5,840,299 A * 11/1998 Bendig et al. ............. 424/133.1

OTHER PUBLICATIONS

Adam et al., "Serum Protein Fingerprinting Coupled with a Pattern-matching Algorithm Distinguishes Prostate Cancer from Benign Prostate Hyperplasia and Healthy Men", Cancer Res. 62:3609-3614 (2002).
Conrads et al., "High-resolution Serum Proteomic Features for Ovarian Cancer Detection", Endocrine-Related Cancer 11:163-178 (2004).
Daly et al., "High-resolution Haplotype Structure in the Human Genome", Nat. Genet. 29:229-32 (2001).
Li et al., "Proteomics and Bioinformatics Approaches for Identification of Serum Biomarkers to Detect Breast Cancer", Clin. Chem. 48:1296-1304 (2002).
Petricoin et al., "Use of Proteomic Patterns in Serum to Identify Ovarian Cancer", Lancet. 359:572-577 (2002).
Valerio et al., "Serum Protein Profiles of Patients with Pancreatic Cancer and Chronic Pancreatitis: Searching for a Diagnostic Protein Pattern", Rapid Commun. Mass. Spectro. 15:2420-2425 ( 2001).
Wright et al., "Proteinchip Surface Enhanced Laser Desorption Ionization (SELDI) Mass Spectrometry: A Novel Protein Biochip Technology for Detection of Prostate Cancer Biomarkers in Complex Protein Mixtures", Prostate Cancer Prostatic. Dis. 2:264-276 (1999).

* cited by examiner

*Primary Examiner*—Marjorie Moran
*Assistant Examiner*—Jason M Sims

(57) ABSTRACT

The present invention relates to a computationally efficient method of finding patterns in any data that can be expressed in the form of arrays of binary features or arrays of categorical features. This includes data represented by continuous-valued attributes that can be transformed to a categorical representation, such as the discovery of patterns of genetic variability that may be causally related to diseases or traits, as well as the discovery of patterns of protein biomarkers that may be used for medical diagnostics, prognostics, and therapeutics. The invention further relates to a program storage device having instructions for controlling a computer system to perform the methods, and to a program storage device containing data structures used in the practice of the methods.

4 Claims, 23 Drawing Sheets

METHOD AND APPARATUS FOR DISCOVERING PATTERNS IN BINARY OR CATEGORICAL DATA

CROSS-REFERENCE TO RELATED APPLICATIONS

This application claims benefit under 35 U.S.C. §119 of the priority of U.S. Provisional Patent Application No. 60/508,825, filed Oct. 3, 2003, which is hereby incorporated by reference in its entirety.

BACKGROUND OF THE INVENTION

Advances in biological and computational methods are providing numerous opportunities for improving human health. Two areas of particular importance include genomic and proteomic variation. Human beings, like members of many species, share a remarkable degree of genetic similarity. It is estimated that the DNA of any two people chosen at random is near 99.9% identical. It is the variation of the remaining ~0.1 % that is responsible for heritable traits that confer upon us our individually recognizable features such as hair/eye/skin color, body shape and size, facial characteristics, personality traits, and so forth. In addition to these rather obvious distinguishing features, the genetic variations referred to above also confer upon us certain other characteristics, some desirable and others not so, such as susceptibility to certain specific diseases (e.g. cancer, heart disease, diabetes, etc.), or conversely, traits which may help to protect us from some diseases (e.g. genetically low cholesterol which may help protect us from cardiovascular disease).

The recent sequencing and publication of the entire human genome, as discussed for example by Collins, F. S., et al. (1987, Cytogenet. Cell Genet. 46:597), has set the stage for a level of understanding of causes and cures for many human diseases not heretofore possible. There are many diseases which have undisputed genetic factors, yet for which the specific genes or combinations of genes remain undiscovered. The reason is in part due to the fact that some diseases have essentially monogenic bases. This means that there is a single gene that is essentially responsible for the disease. Individuals who carry the gene have a high likelihood of contracting the disease. In contrast, many more diseases are presumably polygenic in origin, meaning that there are two or more (possibly many) genes whose simultaneous presence, and possible interactions, are required to cause the disease. The discovery of these polygenic systems will be facilitated by the results from the completion of sequencing of the human genome and by the present invention, as described herein.

Since the human genome appears to be highly similar across individuals, it is of interest to determine the nature of the variations from one individual to another. Research has determined that genetic variations tend to occur at individual nucleotides, rather than over large lengths of nucleotides. These variations have come to be known as Single Nucleotide Polymorphisms, or "SNPs". Moreover, most genetic variations do not seem to occur at arbitrary locations, but at relatively highly-conserved locations spread (not necessarily uniformly) over the genome on the order of once in every few hundred to few thousand locations. In one aspect, this opens the possibility of creating a SNP map by comparing the genomes of several (or many) individuals. If the intervening conserved nucleotides are ignored, then the remaining SNPs represent the actual differences among individuals. This is significant from a computational perspective since this reduces the number of locations to be processed from approximately three billion for the entire genome to perhaps a few million for only the SNPs. It is now possible to see how the knowledge of the sequence of the human genome is significant: it represents, among other things, a constant reference against which the genomes of individuals may be compared to determine sites of polymorphism.

Until the present invention, most methods of SNP analyses rely on determining Linkage Disequilibrium (LD) among SNPs, as described for example by Reich et al. (2001, Nature 411:199-204). LD is essentially a measure of non-randomness in the distribution of alleles among individuals. In population genetics studies, genetically homogeneous populations are used specifically to limit sources of genetic variation and thus focus attention on factors responsible for disease. In contrast, participants in drug trials are genetically much more heterogeneous, making perception of causal genetic factors more difficult; individual SNPs have insufficient correlation with phenotype (disease, drug response, adverse reaction) to be easily detected. In any case, a key limitation of most methods of determining LD is that SNPs are compared in a pairwise fashion. Extended relationships among arbitrary numbers of SNPs are still very difficult to determine. Patterns of SNPs on the other hand should be significantly more specifically correlated with phenotype than any of the individual SNPs comprising them. This is the subject of the present invention, in part, disclosed in more detail elsewhere herein.

Another method that is used to render LD calculations tractable is the use of a so-called "candidate gene" approach, wherein SNPs within a local region of a chromosome or SNPs within genes that are thought to act together (e.g. on the basis of biochemical pathway analysis) are compared. Such an analysis can be thought of as being model-driven, in that it is presumed a priori that certain genes comprise the pool of possible interactions based upon some model—in this case for example those genes within a certain locale in a chromosome, or those genes that are known to interact by means of their participation in a common biochemical pathway. Clearly, there may be circumstances that violate these model assumptions. Any method that restricts analysis to only those genes consistent with the model will be blind to combinations of polymorphisms that lie outside the scope of the model. Conversely, an analysis method that is model-independent and capable of examining all possible interactions will be able to find unforeseen (i.e. un-modeled) interactions.

Due in part to familial relationships through generations (i.e. the fact that relationships among individuals are not strictly random but are to some extent correlated) it will be appreciated that certain patterns of polymorphisms tend to recur. These recognizable patterns are referred to as "haplotypes". Methods used to discover patterns have been described, for example, by Hitt et al. (U.S. patent application Publication No. US2003/0004402A1) and Wall et al. (U.S. patent application Publication No. US2004/0052412A1). It has further been shown by Daly et al. (2001, Nat. Genet. 29:229-32), that in some cases SNPs within a certain locale tend to be correlated. This leads to the concept of a "haplotype block", in which the SNPs within the block take on a small number of the possible permutations. For example, it has been shown in some cases that, though there may be thousands of theoretically possible SNP permutations within a block, only a handful are actually observed. This has to do with the molecular mechanisms underlying genetic variation.

In the area of proteomics, serum biomarkers provide an attractive method of screening for disease since they are non-invasive and relatively inexpensive. Such tests can also be used as adjuncts to other screening or diagnostic tests and help establish prognosis, response to therapy, and risk of recurrence. Although sensitive cancer diagnostics based on biological fluids have great potential, only a handful of useful serological tumor markers have been identified so far. One of the most successful tumor markers identified so far is PSA (Mikolajczyk et al., 2000, Cancer Res. 60:756-759; Bangma et al., 1995, Urology 46:779-784). Other serum markers include CEA (carcinoembryonic antigen), CA19-9 in gastrointestinal tumors, and CA125 in ovarian cancer (Carl et al., 1990, Tumor Biol. 11:88; Kouri et al., 1992, J. Surg. Oncol. 49:78-85; Hunter et al., 1990, Am. J. Obstet. Gynecol. 163: 1164-1167), but these and most other serological markers identified so far are not sufficiently specific. Most known serological markers have so far been discovered in an ad hoc, indirect manner; e.g., proteins observed to be over-expressed in a tumor or secreted into culture medium by tumor cells were subsequently tested in patients' sera. However, this ad hoc, single-protein-at-a-time approach has clearly encountered limited success and is not an optimal strategy.

Recently, proteomic techniques have been successfully applied to identification of changes in protein expression that correlate with early stage cancers. For example, the Surface Enhanced Laser Desorption /Ionization mass spectrometry (SELDI MS) technique was recently used to identify changes in blood protein mass spectra in patients with ovarian cancer (Petricoin et al., 2002, Lancet 359:572-577). Mortality from ovarian cancer is high, often because it is diagnosed at late, incurable stages. The study above showed that the earlier, more curable stages of ovarian cancer are associated with changes in blood protein MS spectra and could form the basis for early detection. However, this study also generated substantial criticism concerning SELDI's limited reproducibility and the fact that it is difficult to identify proteins responsible for diagnostic signals. Despite these concerns, the study clearly demonstrates that: 1) early markers of cancer do exist in serum and 2) the best diagnostics are likely to be patterns of multiple markers (biosignatures) rather than single proteins.

In similar studies, SELDI MS has been used to distinguish control subjects from patients with prostate cancer (Wright et al., 1999, Prostate Cancer Prostatic. Dis. 2:264-276; Adam et al., 2002, Cancer Res. 62:3609-3614), pancreatic cancer (Valerio et al., 2001, Rapid Commun. Mass Spectrom. 15:2420-2425), and breast cancer (Li et al., 2002, Clin. Chem. 48:1296-1304).

Existing analysis methods have proven effective in detecting causes of monogenic diseases, but polygenic diseases are far more complex because varying multiples of interacting genes are responsible for the disease. Whole-genome pattern discovery finds correlated SNPs regardless of genomic distance and therefore can detect these gene interactions. This capability will greatly accelerate the exploitation of the genome for healthcare purposes.

The successful and efficient use of extensive genomic and proteomic data, as well as the successful and beneficial application of such data to the diagnosis, treatment, and therapeutic benefit of humans, as well as other animals, requires methods that can both identify and resolve patterns, conflicts and signals within such data. The present invention meets these needs.

BRIEF SUMMARY OF THE INVENTION

In one embodiment, the invention features a program storage device readable by a machine, the program storage device tangibly embodying a program of instructions executable by a machine to perform a method for finding at least one pattern in one or more binary sequences, the method including translating a set of instances of binary sequences comprising first and second binary values to a list of position indices of first binary values, the position indices corresponding to the location of each of the first binary values within the binary sequences, wherein the second binary values are implicitly represented by the absence of an index corresponding to the position of each of the second binary values.

The method specified by an embodied program further includes forming all unique subsets comprised of pairs of instances, corresponding to support k equal to 2, wherein k represents the number of instances in the subset; finding patterns on the k=2 subsets, the patterns being the result of the application of the Boolean AND operator upon the instances in the subset, the result of which is a list of position indices common to the instances in the subset.

The method specified by an embodied program further provides that, if more than one subset produces identical copies of a pattern, all but one of the subsets, the canonical subset, which has produced a copy of the pattern, are removed from further consideration. Additionally, if a null pattern occurs on a subset, the subset is removed from further consideration.

The method specified by an embodied program further includes the step, for each remaining k=2 subset of two instances, of forming all possible k=3 subsets that can be formed by combining the remaining instances with the two instances in the k=2 subset without redundantly forming the same k=3 subset more than once, setting k=3 and repeating the steps of finding patterns on the k subsets and removing subsets as described above, repeating the steps of setting k=k+1 and inding patterns on the k subsets and removing subsets as described above for successively higher values of k until no more unique subsets of instances can be formed, wherein the resulting patterns correspond to the subset of maximum support k on which each of the resulting patterns has occurred.

In one aspect, the present invention features a method for finding at least one pattern in one or more binary sequences, the method existing independently of a program storage device.

The present invention also features a program storage device readable by a machine, tangibly embodying a program of instructions executable by the machine to perform a method for finding at least one pattern in categorical data, the categorical data being comprised of a set of instances, each of the instances being described by a predefined set of attributes, each of the attributes comprising a predetermined number of allowable categories. The method includes translating the categorical representation of the instances to an equivalent binary representation by assigning, for each attribute, a set of bits, the number of sets of bits equal to the number of categories that exists for the attribute, by means of a mapping function and combining the collection of said bits together into a single binary sequence for each instance, retaining the ability to translate said single binary sequence back to the original categorical representation by means of a multiplicity of inverse mapping functions, one for each said attribute.

The program method further includes finding all binary patterns in the binary representation using a binary-based method of pattern discovery according to the present invention, and translating the binary patterns back to a corresponding categorical representation by means of inverse mapping functions.

In one aspect, the present invention features a method for finding at least one pattern in categorical data, the method existing independently of a program storage device.

The present invention also features a program storage device readable by a machine, tangibly embodying a program of instructions executable by the machine to perform a method for finding patterns of genetic variability. The method specified by an embodied program includes processing one or more polynucleotide sequences, the sequences comprising a unique representation for each of the unique bases comprising a polynucleotide, eliminating representations in the sequences that do not vary across individuals, leaving only the variable representations and forming a corresponding set of reduced sequences of representations, considering each representation in the set of reduced sequences of representations to be an attribute, each attribute having a unique category for each of the unique representations, and applying the method of pattern discovery for categorical data according to the present invention to the resulting set of instances.

In one aspect of the invention, a method specified by an embodied program further includes a step wherein, when more than one of a particular binary value occurs within any group of bits, the possibility exists for ambiguity of more than one of any of a unique base being present at a particular corresponding location in a sequence of symbols. In another aspect of the invention, a method specified by an embodied program provides for the substitution of a unique symbol for each of one or more entire haplotype blocks identified by the method, each of the unique symbols encoding a specific combination of genomic symbols within the haplotype blocks. In still another aspect of the invention, a method specified by an embodied program provides that the number of categories corresponding to one or more of the haplotype blocks can be a value selected from the group consisting of less than 4, equal to 4, or greater than 4. In yet another aspect, each of the haplotype blocks comprises one or more genetic polymorphisms.

In one aspect, the present invention features a method for finding patterns of genetic variability, the method existing independently of a program storage device.

The present invention features a program storage device, wherein the method specified by a program embodied therein further comprises the step of reporting each of the resulting patterns on an output means such as a printer or a program storage device exactly once.

The present invention also features a program storage device readable by a machine, the program storage device tangibly embodying a program of instructions executable by a machine to perform a method of identifying at least one pattern in a set of continuous-valued data. The method specified by the embodied program includes translating a continuous-valued signal into a categorical representation, translating the categorical representation of said instances to an equivalent binary representation, finding all binary patterns in the binary representation by using a binary-based pattern discovery method of the present invention, and translating the binary patterns back to a corresponding categorical representation by means of inverse mapping functions. In one aspect of the invention, continuous-valued data is mass spectrometric data. In another aspect of the invention, continuous-valued data is multi-dimensional gel electrophoresis data.

In one aspect, the present invention features a method for finding at least one pattern in continuous-valued data, the method existing independently of a program storage device.

In one aspect, a method of the invention is useful for identifying patterns in arbitrary categorical alphabets. In another aspect, a method of the invention is useful for identifying patterns in continuous-valued signals. In yet another aspect, a method of the invention is useful for identifying patterns on every subset of a set of instances.

The present invention features a method for identification of at least one pattern in binary sequences, the method comprising the steps of translating a set of instances of binary sequences of 1's and 0's to a list of position indices of said 1's, the position indices corresponding to the location of the 1's within the binary sequences, wherein the 0's are implicitly represented by the absence of an index corresponding to the position of each "0."

The method specified by an embodied program further includes forming all unique subsets comprised of pairs of instances, corresponding to support k equal to 2, wherein k represents the number of instances in the subset; finding patterns on the k=2 subsets, the patterns being the result of the application of the Boolean AND operator upon the instances in the subset, the result of which is a list of position indices common to the instances in the subset.

The method specified by an embodied program further provides that, if more than one subset produces identical copies of a pattern, all but one of the subsets, the canonical subset, which has produced a copy of the pattern, are removed from further consideration. Additionally, if a null pattern occurs on a subset, the subset is removed from further consideration.

The method specified by an embodied program further includes the step, for each remaining k=2 subset of two instances, of forming all possible k=3 subsets that can be formed by combining the remaining instances with the two instances in the k=2 subset without redundantly forming the same k=3 subset more than once, setting k=3 and repeating the steps of finding patterns on the k subsets and removing subsets as described above, repeating the steps of setting k=k+1 and inding patterns on the k subsets and removing subsets as described above for successively higher values of k until no more unique subsets of instances can be formed, wherein the resulting patterns correspond to the subset of maximum support k on which each of the resulting patterns has occurred.

In one aspect, the present invention features a program storage device readable by a machine, the program storage device containing a program specifying a method of the invention, tangibly embodied therein.

In another aspect, the present invention includes a method wherein translating of data is conducted so as to create a sparse bit representation.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

DETAILED DESCRIPTION OF THE INVENTION

Definitions

Figure 1:
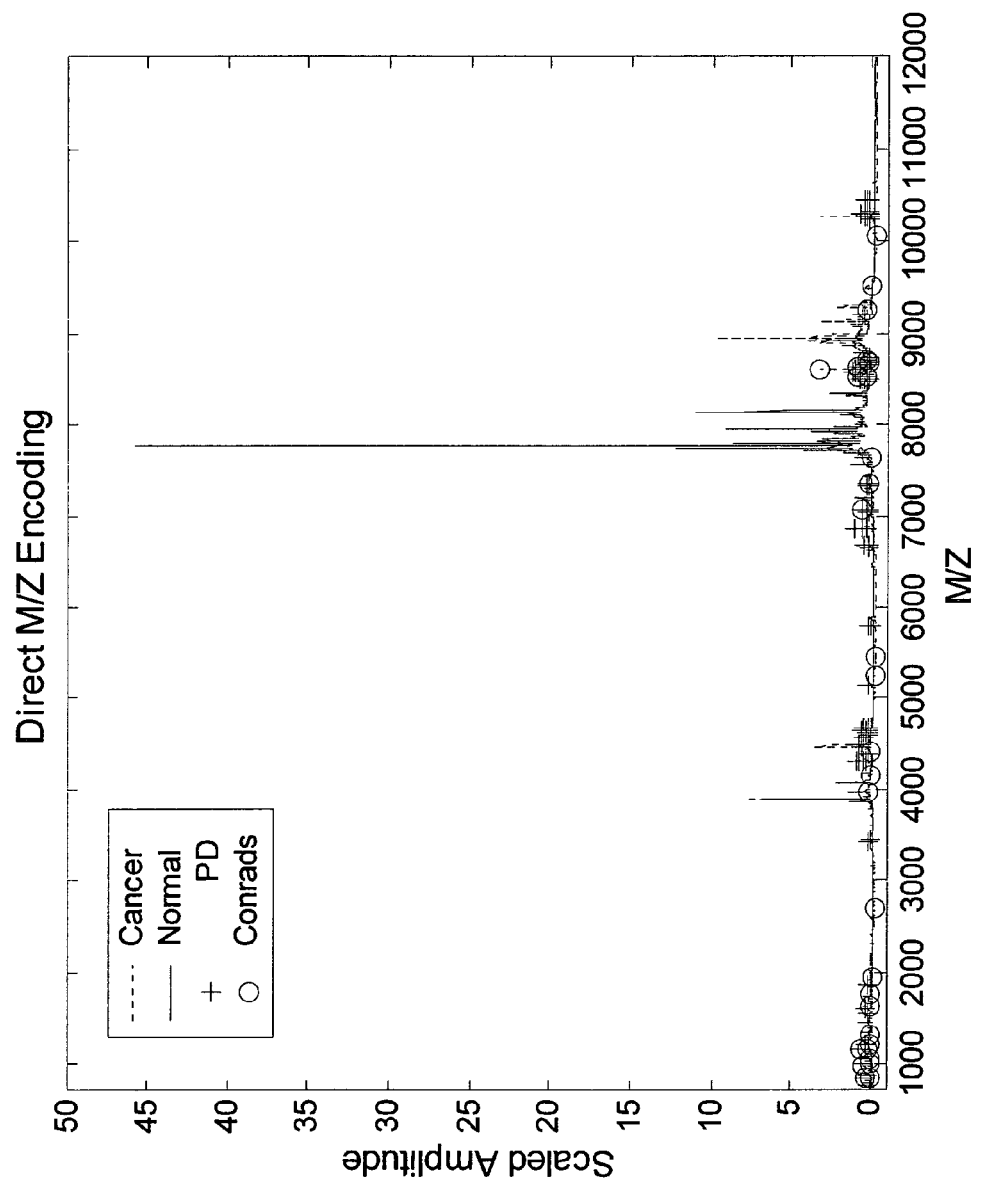
FIG. 1 is a graph illustrating discovered patterns obtained using a direct-encoding method, with cumulative binning, for the entire M/Z range of mass spectrometric data. Patterns are superimposed upon averaged signals for cancer and normal cases. The X-axis represents the M/Z value of the data; the Y-axis represents the scaled amplitude of the data; dashed lines represent data from cancerous cells; solid lines represent data from normal cells; "plus" signs represent pattern discovery data obtained using methods of the present invention; circles represent data obtained by Conrads, et al. ((2004, Endocrine-Related Cancer 11:163-178).

Unless defined otherwise, all technical terms used herein generally have the same meaning as commonly understood by one of ordinary skill in the art to which this invention belongs. Generally, the nomenclature used herein is that well known and commonly employed in the art.

The articles "a" and "an" are used herein to refer to one or to more than one (i.e., to at least one) of the grammatical object of the article. By way of example, "an element" means one element or more than one element.

A "haplotype" refers to a marker. For example, a haplotype may be a pattern of genetic polymorphisms.

A "haplotype block," as the term is used herein, is a set of contiguous markers that are highly inter-correlated across a population.

A "marker," as the term is used herein, refers to a characteristic that identifies the presence of a particular feature. For example, a specific genetic polymorphism can be used as a marker for a particular disease, provided that the specific genetic polymorphism that results in an aberrant polynucleotide sequence in a gene is known to be associated with that particular disease.

A "program storage device" refers to a physical device capable of storing, encoding or tangibly embodying information, such as an instruction or a series of instructions, such as a computer program, and from which device the instruction or series of instructions can be read. Examples of program storage devices include hard disk drives, floppy disks, compact discs, digital video discs, optical disks, flash memory cards, random access memory, read only memory, and magnetic tape.

A program storage device is therefore "readable" if the information stored thereon can be identified or utilized by another device.

A "machine" refers to a device that is useful for performing a desired function. For example, a floppy disk drive is a machine that is useful for reading information contained within a floppy disk program storage device.

An "index," as the term is used herein, refers to a representation of a value, quantity, or characteristic. A "position index" refers to a representation of a location or organization of a value, quantity, or characteristic.

An "attribute," as the term is used herein, is a feature or a characteristic.

A "binary digit" is used synonymously herein with the term "bit," and refers to a unit of information that may exist as one of two possible values. For example, a bit of information representing the state of a light switch may be identified by the term "on" or the term "off."

A "representation," as the term is used herein, refers to a graphic, textual, or numerical symbol that refers to another graphic, letter, word, number, idea, concept, theory, or the like. For example, the letter "A" may be a representation of the nucleotide "ATP" or the base "adenine." Similarly, the term "adenine" may represent itself, in which case the representation is also an identity.

"Polynucleotide," as the term is used herein, refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g, as a cDNA or a genomic or cDNA fragment produced by PCR or restriction enzyme digestion) independent of other sequences. It also includes a recombinant DNA which is part of a hybrid gene encoding additional polypeptide sequence. Further, the term "polynucleotide," as used herein, also refers to genomic DNA, or DNA that has not been isolated from a naturally-occurring state.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

Description

The methods described in the present invention represent a "top-down" approach to complete, deterministic pattern discovery. A method of the present invention first finds the most specific patterns in a set of data that occur between pairs of instances. It then generalizes these patterns by finding only the portions of the patterns that also occur in a third instance. This generates all possible patterns among all triples of instances. The procedure is continued, adding an instance and retaining the portion of the pattern that occurs on the new, larger set of instances. Thus, at the end of the pattern discovery process, all possible patterns have been discovered that occur on all possible combinations of instances. While the number of possible combinations of instances is exponential in the number of instances, as will be described in detail elsewhere herein, the "top-down" procedure of the invention is possible because it is not necessary to examine most of the combinations of instances since, at some point in the procedure, a set of instances has no patterns and thus, all other, higher support, combinations involving this same set of instances do not need to be examined.

A method of the present invention is in contrast to other complete and deterministic methods heretofore known in the art, which start with general (short) patterns that occur in a large number of instances and make more specific (larger) patterns that match in fewer instances.

A fundamental level of a method of the present invention is pattern discovery in a set of fixed length, binary (i.e., "two symbol alphabet") instances. At this level, the presence or absence of a feature at a specific location within an instance may be indicated by one of two values, for example, "0/1" or "false/true." At this level, the operation of finding patterns corresponds to the logical operation, "AND." The method is particularly efficient for sparse inputs. That is, input instances have a small number of features of one value ("true" or 1 for example) and a large number of features with the other value ("false" or 0 for example).

Therefore, the present invention provides methods and apparatuses for discovering patterns in binary or categorical data. The present invention features a method for Pattern Discovery (referred to herein as PD). A novel form of pattern discovery within categorical data, the method for which is disclosed herein for the first time, is also known as Categorical Pattern Discovery (or CPD). CPD is used in conjunction with novel methods for encoding data that may be binary, categorical, or continuous-valued, so as to render them amenable to analysis with PD.

PD describes a family of methods in the category of knowledge discovery/data mining, which itself has been defined by Fayyad et al. (1996, Knowledge Discovery and Data Mining, 1-34), as "the non-trivial process of identifying valid, novel, potentially useful, and ultimately understandable patterns in data." Within this category, PD is unique in that it discovers relationships among input data and builds models based on the resulting ensembles of related inputs. It does not require the hypothesis of an a priori model. This is a distinct advantage in the analysis of complex systems (such as biology) in which the prior proposition of a model is often motivated by intuition, and is often incorrect. Therefore, in one embodiment, the present invention provides a method of pattern discovery that does not rely upon an a priori model.

Figure 23:
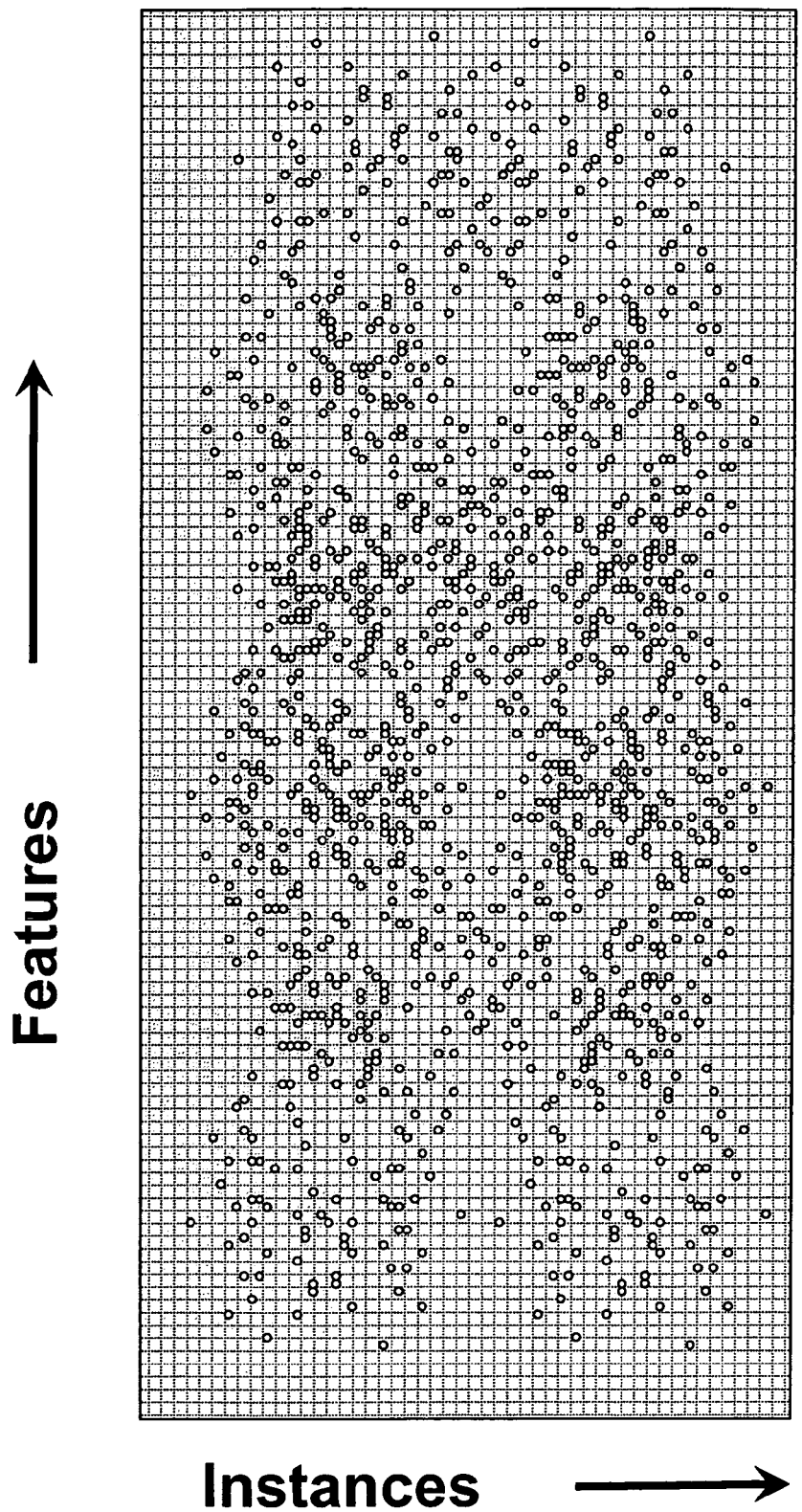
FIG. 23 is a graph illustrating a schematic representation of a set of observations. Observations are represented as a rectangular array wherein each instance is represented by a row. Column values (0 or 1) indicate the presence or absence of the corresponding feature.

Data describing a set of observations is often represented as a rectangular array as shown in FIG. 23, wherein each observation (or instance) is represented by a row, while the features describing the instances are represented by columns. For binary data, the column value (1 or 0) indicates the presence or absence of the corresponding feature. Categorical and continuous-valued data may be encoded as sets of binary features. Patterns in data are sets of features that occur in two or more instances.

Data of the type illustrated in FIG. 23 is often categorized into two or more subgroups. A common task is to use known subgroups of a given population to create an empirical model capable of predicting the classification of unknown instances. For example, the data may represent patients with and without a genetically inherited disease or trait. Therefore, in one embodiment of the invention, the instances shown in FIG. 23 represent people and the features represent single nucleotide polymorphisms. Another example is data that may be used to develop a medical diagnostic. In this embodiment of the invention, instances represent blood samples drawn from a population of patients and features represent the abundance of proteins or peptide fragments found in the blood through techniques such as two-dimensional ("2D") gel electrophoresis or mass spectrometry.

Common techniques used to build empirical models from data sets in order to make predictions on unknown instances often utilize individual measured features. These features are generally ranked based on how informative they are with respect to a classification and then combined in linear or non-linear models. However, methods utilizing individual features overlook the possibility that combinations of relatively uninformative features may, in fact, be more informative than the most informative individual features. This is likely to be the case in high dimensional data involving thousands of features. The key problem in finding an optimal set of patterns for classification is computational complexity.

If the instances of a dataset are described by n features and one considers potential patterns of two or more of these features, then there are $2^n$-n-1 possible combinations. For a relatively small problem involving 5 features, the number of combinations is only 26 which allows for an optimal solution through an exhaustive search. However, even for relatively modest problems involving 100 features, exhaustive search methods are infeasible since the number of combinations is over $10^{30}$. For many practical problems the number of features can be in excess of 10,000 which lead to over $10^{3010}$ possible combinations of features to consider. Thus, in order to solve the pattern discovery problem for such high dimensional problems, most methods employ heuristic search techniques such as genetic algorithms. These methods randomly select a few features at a time and iterate to find a solution that may or may not be optimal. More useful methods for application to high-dimensional problems include those that are complete and deterministic, such as those described by Rigoutsos et al. (1998, Bioinformatics 14:55-57) and Califano (2000, Bioinformatics 16:341-357).

On the contrary, the method of pattern discovery described in the present invention for the first time is complete and deterministic, and further, is the first implementation for binary, categorical, and continuous-valued data that discovers patterns by starting with combinations of two instances; then combining a third instance, and so on, as described in greater detail elsewhere herein. That is, the present invention finds all patterns that exist in every possible subset of the data being examined. The feasibility of the present approach is based on the observation that, while there are an exponential number of possible combinations of instances, patterns do not exist on the majority of them. By efficiently eliminating from consideration sets of instances that do not contain patterns, a method of the present invention finds the complete set of patterns that exists for a given data set without exploring all possible combinations, and without the need to do so. Therefore, in the present invention, it has be found empirically, for the first time, that for problems of practical interest, the methods described herein have computational complexity that scales cubically with the number of features.

A key advantage of the present invention is that all possible patterns are identified for every possible subset of the set of input "instances." This completeness of discovered patterns, demonstrated for the first time herein, enables every possible clustering of training data to contribute to empirical models used to predict unknown instances. By way of a non-limiting example, a large diverse population may have the same disease, however, a diagnosis based on the measurement of several proteins in blood samples may require the use of different sets of proteins for different subpopulations of diseased individuals. When armed with the disclosure set forth herein, the skilled artisan will now be able to discover patterns for every partitioning of input instances, as the present invention properly takes into account the diversity of subpopulations.

The factors differentiating subpopulations may not be known, however, since all patterns on all possible subsets of input instances are discovered, no prior knowledge or subdivision of the input data is necessary. That is, according to the present invention, extra steps previously required for pattern analysis will become redundant and are no longer required, saving both time and cost. Thus, in one embodiment of the present invention, empirical models based on complete sets of patterns will have fewer false negatives (i.e., greater sensitivity) than methods based on a monolithic representation of the input data.

In an embodiment of the present invention, high specificity (i.e., few false positives) is attained by utilizing training data to filter patterns based on their association with known categories. As described elsewhere herein, patterns comprised of multiple features have greater predictive power than single features combined through linear or non-linear models. Thus, the complete set of patterns discovered with the present invention can be used to construct optimal empirical models with greater predicative power than methods utilizing models built from combinations of individual features (such as decision trees, linear regression, or neural networks) or models built with patterns discovered through heuristic search methods such as genetic algorithms.

In one aspect of the present invention, the data comprising the input to pattern discovery corresponds to a set S of N individual instances. For genomic data, by way of a non-limiting example, each member $S_i$ of S is comprised of a string of approximately $3 \times 10^9$ symbols in the alphabet $\Sigma = \{A, G, C, T\}$ corresponding to the identities of the four different nucleotides comprising DNA.

As described elsewhere herein, a method of the present invention is complete and deterministic, and the "completeness" of discovered patterns resulting from a method of the present invention enables every possible clustering of training data to contribute to empirical models used to predict unknown instances. Therefore, in one embodiment, the present invention features a method for the identification of patterns in binary sequences. A method of the invention includes the steps of translating a set of instances of binary sequences, represented generically by the two binary values "x" and "y," to a list of position indices of said x's, wherein the position indices correspond to the location of the x's within the binary sequences, and the y's are implicitly represented by the absence of an index corresponding to the position of each "y." It will be understood that the value of the bits may be "1" and "0," as is commonly known in the art. However, as will be understood by the skilled artisan, a binary representation may consist of any two values, digits, terms, identifiers, or the like, and may be arbitrarily defined.

The method of the invention further includes the steps of forming all unique subsets having pairs of instances, corresponding to a support, "k,"equal to 2, wherein the support is defined as the number of instances in the subset, and identifying patterns on the k=2 subsets, wherein the patterns occur as the result of the application of a Boolean "AND" operator upon the instances in the subset, the result of which is a list of position indices common to the instances in the subset.

The method further includes the step of removing from further consideration all but one of the subsets obtained in a previous step of the invention, referred to as the canonical subset, which has produced a copy of the pattern, if more than one subset produces identical copies of a pattern. In the method of the invention, if a pattern that contains no position indices—a "null" pattern—occurs on a subset, the pattern is removed from the subset and from further consideration. For each remaining k=2 subset of two instances, all possible k=3 subsets that can be made are formed by combining the remaining instances with the two instances in the k=2 subset without redundantly forming the same k=3 subset more than once, then setting k=3 and repeating a method of the invention beginning with the step at which patterns are identified on the k=2 subsets.

The method of the invention subsequently includes the step of a repetition, for each remaining k=n subset of n instances, all possible k=n+1 instances that can be made by combining the remaining instances with the n instances in the k=n subset without redundantly forming the same k=n+1 subset more than once, with the repetition continued for successively higher values of k until no more unique subsets of instances can be formed. Each of the resulting patterns corresponds to the subset of maximum support ("k") on which each of said patterns has occurred.

In another embodiment, the present invention features a method of identifying patterns in categorical data, wherein the categorical data is comprised of a set of instances, with each instance described by a predefined set of attributes and each attribute comprise of a predetermined number of allowable categories. Such a method includes the step of translating the categorical representation of instances to. an equivalent binary representation.

For categorical data, features are described by a "multi-valued alphabet." By way of a simplified example, a description of a parking lot full of cars represents data and the features are represented as color (i.e., red/green/blue) and style (i.e., coupe/sedan/convertible). In one embodiment of the present invention, genetic sequence data is set forth as one type of categorical data, in which the instances are sequenced genomes (or variations in genomes, SNP's) and the alphabet is the code used for DNA (A/C/T/G). According to the present invention, a method by which categorical data is transformed into binary form utilizes four binary place holders (for DNA, in this example), only one of which is typically set to indicate the value of the categorical variable. However, this method allows an even more general representation of categorical data in that if two place holders are set, values can be represented that may reflect an ambiguous value. Categortical data is similar to binary data in that there is no inherent relationship between the possible values for an attribute. For example, "green" is neither larger nor smaller than "red."

According to a method of the present invention, translation of the categorical representation is accomplished by assigning, for each attribute, a set of bits, the value of each of the bits represented generically herein as either "x" or "y," the number of which is equal to the number of categories that exists for the attribute, by means of a mapping function, and then combining the collection of bits together into a single binary sequence for each instance, retaining the ability to translate any single binary sequence back to the original categorical representation by means of a multiplicity of inverse mapping functions, one for each attribute. It will be understood that the value of the bits may be "1" and "0," as is commonly known in the art. However, as will be understood by the skilled artisan, a binary representation may consist of any two values, digits, terms, identifiers, or the like, and may be arbitrarily defined.

The method of the invention further includes finding all binary patterns in the resulting binary representation, using the method of a method of identifying patterns in a binary sequence, as described in detail elsewhere herein, and subsequently, translating the binary patterns back to a corresponding categorical representation by means of an inverse mapping function described above.

In one aspect of the invention, the method is useful for the identification of patterns of genetic variability among two or more subjects. Such a method includes processing a set of genome sequences, wherein the sequences comprise sequences of symbols typically written in the alphabet, such as A, C, G, and T, and wherein processing eliminates symbols in the sequences that do not vary across multiple subjects, leaving only the variable symbols and forming a corresponding set of reduced sequences of symbols. A method of the invention also includes identifying each symbol in a set of reduced sequences of symbols to be an attribute, wherein each attribute comprises four categories according to whether the symbol is an "A," "C," "G." or "T." and subsequently performing pattern identification as described in detail elsewhere herein.

In another embodiment of the invention, the method includes the provision that, when more than one "1" occurs within any group of four bits, the possibility exists for ambiguity of more than one of any of "A" or "C" or "G" or "T" being present at the particular corresponding location or locations in a sequence of symbols. In another embodiment, a method of the invention provides for the substitution of a unique symbol for each of one or more entire haplotype blocks identified by the method, wherein each of the unique symbols encodes a specific combination of genomic symbols within the haplotype blocks. In one aspect, the method includes a provision that the number of categories corresponding to one or more of such haplotype blocks can be a value selected from the group consisting of less than 4, equal to 4, or greater than 4. In yet another aspect, a haplotype block comprises one or more genetic polymorphisms.

A method of the present invention may be practiced or implemented by any means, as will be understood by the skilled artisan, when armed with the disclosure set forth herein. In one embodiment, a method of the invention is practiced using one or more electronic devices. In one aspect, an electronic device is a computer. Computers useful in a method of the present invention include, but are not limited to, electronic computing devices including at least one processor, such as a personal computer, a network server, a workstation, a handheld computer, or a supercomputer.

In another embodiment, a method of the present invention may also be practiced or implemented manually by means including, but not limited to, at least one or a combination of a spreadsheet or a calculator.

In one aspect of the invention, each of the methods described herein is implemented as one or more programs of instructions executed by computer. In a typical realization, such program or programs of instructions can be saved on a mass storage device, such as for example a hard disk drive, a floppy disk drive, or a magnetic tape storage device, or even a plurality of such devices. Thus, the program or programs of instructions may be read in and executed by one or more machines, either serially or in parallel, depending on the data in consideration. Therefore the novelty and utility of both the methods and their implementions are not dependent on any particular embodiment of computer or computers.

The invention therefore also features a program storage device tangibly embodying a program of instructions comprising one or more of the methods described herein. In one aspect of the invention, a program storage device is readable by a machine including, but not limited to a computer.

Therefore, in one embodiment, the present invention features a program storage device tangibly embodying a program of instructions executable by a machine to perform a method for the identification of patterns in binary sequences. Such a program embodied within a program storage device contains instructions for a method of the invention including the steps of translating a set of instances of binary sequences of x's and y's to a list of position indices of said x's, wherein the position indices correspond to the location of the x's within the binary sequences, and the y's are implicitly represented by the absence of an index corresponding to the position of each "y." It will be understood that the value of the bits may be "1" and "0," as is commonly known in the art. However, as will be understood by the skilled artisan, a binary representation may consist of any values, as described in detail elsewhere herein.

The method embodied by a program storage device further includes the steps of forming all unique subsets having pairs of instances, corresponding to a support, "k,"equal to 2, wherein the support is defined as the number of instances in the subset, and identifying patterns on the k=2 subsets, wherein the patterns occur as the result of the application of a Boolean "AND" operator upon the instances in the subset, the result of which is a list of position indices common to the instances in the subset.

The method embodied within a program storage device further includes the step of removing from further consideration all but one of the subsets obtained in a previous step of the invention, referred to as the canonical subset, which has produced a copy of the pattern, if more than one subset produces identical copies of a pattern. In a method of the invention embodied within a program storage device, if a pattern that contains no position indices—a "null" pattern— occurs on a subset, the pattern is removed from the subset and from further consideration. For each remaining k=2 subset of two instances, all possible k=3 subsets that can be made are formed by combining the remaining instances with the two instances in the k=2 subset without redundantly forming the same k=3 subset more than once, then setting k=3 and repeating a method of the invention beginning with the step at which patterns are identified on the k=2 subsets.

The method embodied by a program storage device of the invention subsequently includes the step of a repetition, for each remaining k=n subset of n instances, all possible k=n+1 instances that can be made by combining the remaining instances with the n instances in the k=n subset without redundantly forming the same k=n+1 subset more than once, with the repetition continued for successively higher values of k until no more unique subsets of instances can be formed. Each of the resulting patterns corresponds to the subset of maximum support ("k") on which each of said patterns has occurred.

As will be understood by the skilled artisan, when armed with the disclosure set forth herein, any method of the present invention may be tangibly embodied within a program storage device, wherein the method is embodied as a program of instructions executable by a machine.

In contrast to the present invention, and in principle, it would be possible to discover patterns of symbols, wherein a pattern is defined as a subset of symbols, not necessarily contiguous, that occur in the same relative positions in two or more genomes. However, there are several problems with such an approach. First, the high degree of similarity across genomes will cause the output patterns to be dominated by common elements, where the actual task is to identify significant differences among the genomes. Second, the size and number of output patterns will be large, causing even efficient methods of pattern discovery to require excessive amounts of computer resources, both in terms of time and of space. Lastly, having obtained a large number of large patterns, a post-processing step would be required in order to distinguish "interesting" patterns in the output from "uninteresting" ones. This post-processing step may be predicted to require excessive computer resources as well. The present invention overcomes these problems.

The present invention also features a method for analysis of patterns in spectrometric data. In one embodiment, the invention features a method for analysis of mass spectrometric data. By way of a non-limiting example, for data such as mass spectrometry data, each member $S_i$ of S is comprised of continuous-valued amplitudes corresponding to ion current at specific mass to charge ratios. In general, each member $S_i$ of S could be comprised of binary (2 symbol alphabet), categorical (arbitrary size alphabet), or continuous-valued numbers that will be represented categorically. Thus the data can represent any arbitrary set of instances described by a set of features.

Therefore, the present invention also features methods of analysis of categorical data. In one embodiment, the present invention includes the solution of problems arising in the analysis of categorical data by means of an encoding of the input S so as to emphasize sites of polymorphism (i.e, high variabililty), and then a further encoding of the result so as to render it amenable to categorical pattern discovery, as set forth in greater detail elsewhere herein. This re-encoding process results in the representation of categorical data, including binary native categorical data or continuous-valued data cast into a categorical form, as binary sequences. In one embodiment of the present invention, such binary sequences are defined as strings of "bits" which are either "1's" or "0's", as described in greater detail elsewhere herein.

Therefore, according to the present invention, after re-encoding data, all patterns of the re-encoded features are discovered, using Categorical Pattern Discovery (CPD) as described herein. Importantly, the resultant patterns are subject to the concepts of maximality and "support," as related to maximality. That is, the support of a pattern is the specific set of binary sequences or "instances" that contain the pattern. A maximal pattern therefore is a pattern of 1's and 0's, wherein there are no other patterns with a greater number of 1's that exists with the same support. Once such patterns have been discovered, a large variety of further analysis methods using these patterns may be employed, including but not limited to analysis, empirical modeling, selection, filtering, scoring, ranking and so forth.

Genetic Polymorphism Data

In one embodiment, the present invention is useful for the analysis of genetic polymorphisms. However, it will be understood by the skilled artisan, when armed with the disclosure set forth herein, that the present invention is applicable to any categorical or continuous-valued data. Such categorical data includes, but is not limited to, mass spectrometric data.

In one embodiment of the invention, an analysis of genetic polymorphism data includes the re-encoding of input data. The input S is re-encoded to remove all symbols representing nucleotides which are not polymorphic, leaving a compressed string of symbols representing only the polymorphisms. Then, each of symbols {A, C, G, T} are replaced in order to represent a polymorphism by 4 binary digits, or bits. Each bit of the said four bits being set to the value "1" represents that the corresponding symbol representing a polymorphism is an A, a C, a G, or a T, respectively. A bit value of "0" represents that the polymorphism symbol is not the A, C, G, or T represented by that bit. In the event that the polymorphism is not known unambiguously, more than one of the four bits may be simultaneously set to the value "1".

The resulting transformed input S' of N genomes therefore consists of a set of N binary sequences. The length of each sequence $S'_i$ is the same, and equal to 4M, where M is the number of identified polymorphism sites, the factor of 4 being due to the recoding of SNP data from an alphabet of size 4 symbols to a binary alphabet capable of distinguishing the 4 categories. In one aspect of the invention, the set $S'_i$ may be beneficially viewed as a binary matrix of N rows by 4M columns wherein each row corresponds to the re-coded genome of one individual, and each column represents the presence or absence of a specific categorical feature in that genome, the features being specific nucleotides A, G, C, or T at a specific polymorphism site. As will be understood by the skilled artisan in view of the disclosure set forth herein, this matrix is fairly sparse, which has performance implications for categorical pattern discovery as described below.

In one embodiment of the invention, SNPs occurring in haplotype blocks take on only a small number of the possible permutations within the haplotype block. In one aspect, it is possible to modify the encoding described herein in order to take advantage of such a small number of the possible permutations within the haplotype block. Specifically, each unique combination of SNPs in a haplotype block may be assigned a unique symbol. This process is repeated for each haplotype block. The resulting string of symbols could then be further encoded as described above, the generalization being that the number of columns in the resulting binary matrix will no longer be 4M, but some greater or lesser number that corresponds to the sum of the number of categorical features present in the said string of symbols. In another aspect of the invention, it is also possible to combine these two methods of encoding to account for the possibility that some SNPs occur in haplotype blocks, while others may vary independently of their neighbors.

Regardless of the particular method of re-encoding of the symbol sequences into binary sequences, the next step of the method is to perform CPD. In one embodiment of the invention, all maximal patterns of bits that exist in a set of data are discovered. The resulting set of maximal patterns comprises all patterns of support $\geq 2$, up to the maximum support within the input data. With these patterns in hand it is then possible to utilize these patterns to perform analysis, empirical modeling, selection, filtering, scoring, ranking and the like, as is useful in the determination of the biological significance of combinations of polymorphisms. The determination of the significance of such combinations of polymorphisms is known in the art, and will therefore not be discussed further herein.

In one embodiment of the invention, a method of CPD relies upon the concept that the position of an attribute within the input description is important. This is in contrast for example with pattern discovery as practiced in the analysis of biological sequence data, as described for example in Vaidyanathan et al. (2003, U.S. Patent application Publication No. 20030220771) and Rigoutsos et al. (2002, Bioinformatics 14:55-57). By way of a non-limiting example, in the case of biosequence data, a particular pattern may occur at the beginning, end, middle, or other location within a sequence of symbols. Using a CPD analysis according to the present invention, a pattern of 1's and 0's, for example 100101, is not considered the same pattern in two binary sequences if it does not occupy the identical set of locations in both sequences. This is an important distinction, and is exploited beneficially in the present invention.

As disclosed elsewhere herein, an input comprised of the four categories represented by the alphabet {A,C,G,T} representing nucleotides in DNA can be transformed into a binary representation. Likewise, categories representing observed combinations of genomic variations within a haplotype block, can be similarly transformed into a binary representation, albeit with a number of bits corresponding to the number of such categories required to represent the variations of the haplotype block. Therefore, it will be understood by those skilled in the art, when armed with the present disclosure, that any input comprising a set of instances, with each instance being described by a predefined list of attributes and each attribute having a predetermined number of allowable categories, may be transformed into a binary representation using the method described above for SNPs, haplotypes, or a combination of the two, among others.

In an embodiment of the invention, once the raw data have been transformed from their original categorical representation to a binary representation as described above, patterns of 1's and 0's may be discovered, taking advantage of the fact that the position of a binary digit within the binary string carries the information regarding the significance of that digit. In one aspect of the invention, a binary string is transformed into a list of indices, each of which represents the location of a binary digit whose value is 1. The absence of a given index implicitly represents a 0 at that location. In the event that the number of 1's in the binary array is much smaller than the number of 0's (a condition said to be "sparse") this representation is significantly more compact than explicitly writing out the array as the original string of 1's and 0's.

In one aspect of the present invention, the basic operator for pattern discovery among the instances is the boolean AND operator. In one embodiment, the boolean AND operator, acting upon the combination of two instances, provides a list of position indices common to both instances. In another embodiment, for more than two instances, the result of applying the AND operator on the entire set is equivalent to applying it first to any pair, and then to that result combined with another instance, and so forth, until all instances have been utilized. It will be understood that the order of application of the AND operator is not significant. Further, during this process, if at any time the list of position indices that results from the AND operator shrinks to a length of zero, the resulting pattern is said to be "null".

In one embodiment of the invention, in order to discover all patterns on all combinations of instances (a combination of instances will hereinafter be termed a "subset"), all pairs of instances are first formed, and patterns are discovered that occur on each pair by the means previously disclosed. If the same pattern occurs at more than one such subset, the pattern is recorded on only one of them (which will be referred to as a "canonical subset"). All other subsets are removed from further consideration. If the AND of two instances produces a null pattern it is also removed from further consideration.

For each remaining subset, all non-redundant instances are combined with that subset to form a new group of subsets. It will be appreciated that each of these subsets will be associated with exactly three distinct instances. Furthermore, each 3-instance subset, deriving from a unique 2-instance subset, will be distinct. Again, if a duplicate pattern occurs on more than one such 3-instance subset, all but a single canonical subset are removed from further consideration.

In one aspect of the invention, the process of forming subsets of successively higher support, and finding patterns on subsets, is repeated until all subsets of instances for which non-null patterns exist have been have been formed. A pattern is reported only from the subset of maximum support at which it occurs, thereby insuring that a pattern is reported exactly once, and that it is associated with all of the instances it matches.

As described elsewhere herein, the present method of pattern discovery is particularly efficient for sparse data, since there are fewer sets of instances that have patterns. Specifically, there will be fewer cases of high support patterns. Thus, as described herein, there will be a rapid elimination of combinations of instances that must be examined for patterns. As described elsewhere herein regarding pattern discovery for single nucleotide polymorphisms, the combination of features into haplotype blocks is one means of creating a sparser representation by creating a new, smaller set of categorical variables.

The present invention features multiple ways in which all possible non-redundant k-instance subsets can be formed. A particular subset can be labeled by the ordinality of the instances that comprise that subset. By way of a non-limiting example, the instances may be labeled with an ordinality index 1, 2, 3, . . . , n, where n is the number of instances in the input set. A particular subset corresponding to the first instance combined with the second instance would then be labeled as the (1,2) subset. In order to form all of the k=2 subsets, all pairs (x,y), x=1, 2, . . . , n−1, y=x+1, x+2, . . . , n are formed. Then, given the each of the k=2 subsets, each subset being labeled by unique (x,y) indices, one could form k=3 subsets, labeled (x,y,z), where z=y+1, y+2, . . . , n. The rule set forth by this non-limiting example generalizes to arbitrary k by always adding a new index, the new index always being at least one greater than the previous maximum index.

One embodiment of the present invention is illustrated by the following process of pattern discovery in binary sequences. The following five binary sequences are first considered:
Sequence 0: 111111
Sequence 1: 010101
Sequence 2: 101010
Sequence 3: 111000
Sequence 4: 000111

The explicit binary representation is first transformed to a list of position indices corresponding to the locations of the 1's in each sequence. The convention is used that the first position is labeled 0, the second 1, and so forth:
Sequence 0: 0,1,2,3,4,5
Sequence 1: 1,3,5
Sequence 2: 0,2,4
Sequence 3: 0,1,2
Sequence 4: 3,4,5

From this representation, forming all pairs of sequences, and applying the Boolean AND operator, the resulting patterns are:
Combination [0,1]: 1,3,5
Combination [0,2]: 0,2,4
Combination [0,3]: 0,1,2
Combination [0,4]: 3,4,5
Combination [1,2]: Null
Combination [1,3]: 1 (*)
Combination [1,4]: 3,5 (*)
Combination [2,3]: 0,2 (*)
Combination [2,4]: 4 (*)
Combination [3,4]: Null The combinations with Null patterns are removed from further consideration.

The non-redundant combinations that can be formed from these combinations, and their patterns, are:
Combination [0,1,2]: Null
Combination [0,1,3]: 1
Combination [0,1,4]: 3,5
Combination [0,2,3]: 0,2
Combination [0,2,4]: 4
Combination [0,3,4]: Null
Combination [1,2,3]: not considered
Combination [1,2,4]: not considered
Combination [2,3,4]: Null Combinations [1,2,3] and [1,2,4] are not considered because the previous combination [1,2] was Null. Additionally, comparing these subsets of 3 instances with the previous subsets of 2 instances, we see that [0,1,3] yields the same pattern as [1,3], [0,1,4] yields the same pattern as [1,4], [0,2,3] yields the same pattern as [2,3], and [0,2,4] yields the same pattern as [2,4], which are the support-2 subsets marked with (*). Thus, each of these patterns is reported once and only for the subset of maximum support at which they occur, namely at support 3.

The next set of non-redundant combinations are:
Combination [0,1,2,3]: not considered
Combination [0,1,2,4]: not considered
Combination [0,1,3,4]: Null
Combination [0,2,3,4]: Null
Combination [1,2,3,4]: not considered The only combinations that have to be considered are [0,1,3,4] and [0,2,3,4], and they both turn out to be Null. Thus the entire exhaustive set of maximal patterns associated with the input in this example (written in both position index form and original binary form) comprises:
[0,1]: 1,3,5 010101
[0,2]: 0,2,4 101010
[0,3]: 0,1,2 111000
[0,4]: 3,4,5 000111
[0,1,3]: 1 100000
[0,1,4]: 3,5 000101
[0,2,3]: 0,2 101000
[0,2,4]: 4 000010

The total number of possible combinations in this case of five instances is $2^5-5-1=26$. The number that are actually considered is only 21, leading to a computational savings. For a small illustrative problem such as this one, this is a small savings, but for a larger problem the proportion of combinations actually considered using a method of the present invention will typically be exponentially small, leading to extremely large savings.

To illustrate the concept of a canonical subset, the following, even smaller example is presented. In this embodiment of the invention, for the sake of brevity, the step of conversion from a set of binary sequences to a set of position indices has been omitted:
Sequence 0: 100111
Sequence 1: 010101
Sequence 2: 000101
Sequence 3: 100001
Combination [0,1]: 000101
Combination [0,2]: 000101
Combination [0,3]: 100001
Combination [1,2]: 000101
Combination [1,3]: 000001
Combination [2,3]: 000001

Since combinations [0,1], [0,2], and [1,2] generate the same pattern, one of them, for example [0,1], is designated the canonical subset, and the other two can be eliminated from further consideration. The final pattern on combination [0,1,2] is discovered from the canonical subset [0,1] combined in the next step with instance 2.

The complete set of patterns corresponding to this example are:
Combination [0,3]: 100001
Combination [0,1,2]: 000101
Combination [0,1,2,3]: 000001

The method of re-encoding categorical data such as SNP data is best illustrated by another example. In another embodiment of the invention, it is assumed that each position of a string of symbols representing sites of polymorphism in DNA is represented by one of the four symbols {A,C,G,T}. One such string might be, for example:
ACATTG.

Four bits can then be assigned to each of these positions, each bit indicating presence (1) or absence (0) of the corresponding symbol. It is not important how these bits are arranged so long as their arrangement is recorded so that the resulting pattern may be decoded back into a corresponding string of symbols. Thus, choosing arbitrarily the arrangement that the first four bits correspond to the first symbol in the string, the next four bits correspond to the next symbol in the string, and so forth, and the first bit for each symbol corresponds to an A, the second a C, the third a G, and the fourth a T, the following binary encoding is obtained, shown with spaces inserted to allow the eye to more easily see the transitions between symbols:
1000 0100 1000 0001 0001 0010

A set of binary strings derived in this way from categorical sequences can then be analyzed for binary patterns. The resulting patterns can then be decoded back into a corresponding categorical description.

It will be understood, in view of the disclosure set forth herein, that genetic polymorphism analysis according to a method of the present invention is useful for the diagnosis, characterization or discovery of many diseases, including, but not limited to cancer, neoplasms, musculoskeletal diseases, digestive system diseases, stomatognathic diseases, respiratory tract diseases, otorhinolaryngologic diseases, nervous system diseases, eye diseases, urologic and male genital diseases, female genital diseases and pregnancy complications, cardiovascular diseases, hemic and lymphatic diseases, congenital, hereditary, and neonatal diseases and abnormalities, skin and connective tissue diseases, nutritional and metabolic diseases, endocrine diseases, immunologic diseases and mental disorders, among others.

Other examples of diseases for which the present invention is particularly useful include, but are not limited to, pre-eclampsia, endocrine diseases such as, but not limited to, diabetes, autoimmune diseases (eg. rheumatoid arthritis, multiple sclerosis, juvenile onset diabetes), cardiovascular diseases, pulmonary diseases and acute lung injury, and osteoporosis.

In one embodiment of the invention, a method of the invention is useful for pattern discovery in ovarian cancer. In another embodiment, a method of the invention is useful for pattern discovery in breast cancer. In yet another embodiment, a method of the invention is useful for pattern discovery in lung cancer. Other cancers for which a method of the present invention is useful for the diagnosis, characterization or discovery of include, but are not limited to, acute lymphoblastic leukemia, acute myeloid leukemia, adrenocortical carcinoma, AIDS-related cancers, AIDS-related lymphoma, anal cancer, basal cell carcinoma, bile duct cancer, bladder cancer, bone cancer, brain cancers (eg. brain stem glioma, cerebellar astrocytoma, ependymoma, medulloblastoma, supratentorial primitive neuroectodermal), breast cancer, bronchial adenomas/carcinoids, burkitt's lymphoma, central nervous system lymphoma, cerebellar astrocytoma, cervical cancer, chronic lymphocytic leukemia, chronic myelogenous leukemia, chronic myeloproliferative disorders, colorectal cancer, cutaneous T-cell lymphoma, endometrial uterine cancer, ependymoma, esophageal cancer, extragonadal germ cell tumor, extrahepatic bile duct cancer, eye cancer (eg. intraocular melanoma, retioblastoma), gallbladder cancer, gastrointestinal carcinoid tumor, germ cell tumor (extragonadal), germ cell tumor (ovarian), gestational trophoblastic tumor, glioma, hairy cell leukemia, head and neck cancer, hodgkin's lymphoma, hypopharyngeal cancer, hypothalamic and visual pathway glioma, islet cell carcinoma, Kaposi's sarcoma, kidney cancer, laryngeal cancer, lip and oral cavity cancer, liver cancer, lung cancer (eg. non-small cell, small cell), malignant fibrous histiocytoma of bone/osteosarcoma, medulloblastoma, melanoma, merkel cell carcinoma, mesothelioma, multiple myeloma, mycosis fungoides, myelodysplastic syndromes, myelogenous leukemia, chronic myeloid leukemia, myeloproliferative disorders, chronic nasal cavity and paranasal sinus cancer, nasopharyngeal cancer, neuroblastoma, non-hodgkin's lymphoma, oral cavity cancer, lip cancer, oropharyngeal cancer, osteosarcoma, ovarian cancer, ovarian epithelial cancer, ovarian germ cell tumor, ovarian low malignant potential tumor, pancreatic cancer, paranasal sinus and nasal cavity cancer, parathyroid cancer, penile cancer, pheochromocytoma, pineoblastoma and supratentorial primitive neuroectodermal tumors, pituitary tumor, pleuropulmonary blastoma, primary central nervous system lymphoma, prostate cancer, rectal cancer, retinoblastoma, rhabdomyosarcoma, salivary gland cancer, sezary syndrome, skin cancer (non-melanoma), small intestine cancer, soft tissue sarcoma, squamous cell carcinoma, stomach (gastric) cancer, testicular cancer, thymoma and thymic carcinoma, thyroid cancer, trophoblastic tumor, urethral cancer, uterine sarcoma, vaginal cancer, vulvar cancer, and Wilms' tumor, among others.

It will also be understood, based in part on the disclosure set forth herein, that diagnosis and characterization of diseases according to a method of the present invention is useful for proteomic data as well as genomic data.

In an embodiment of the invention, analysis using a pattern discovery method of the present invention is useful in pharmaceutical applications such as, but not limited to, predicting which patients will respond to a drug or will experience drug toxicity. Such an application of the present invention is useful in partitioning patient populations in clinical trials. In another embodiment, a method of the present invention is useful for combination of a diagnostic test with drug treatment to predict or monitor drug effectiveness or adverse response. In yet another embodiment, a method of the invention is useful to help discover new drug targets for the pharmaceutical industry. In still another embodiment, a method of the invention is useful for animal studies and to create animal models for disease or drug response.

As will be understood by one of skill in the art, a pattern discovery method of the present invention may be applicable to disciplines outside of pharmaceuticals and biologically-related research. The present invention is applicable to analysis in areas such as, but not limited to, financial data, textual data, electronic information, such as spam filters, among others.

General Categorical Data

General categorical data useful in the present invention is similar to that described elsewhere herein, except that each feature may be described by an alphabet of symbols of any size. For example, in English text, the alphabet can be considered to consist of the 26 letters along with symbols for spacing and punctuation. By way of a non-limiting example, a convenient form might be the ASCII representation of 256 symbols used to represent text on computers. The reduction of this arbitrary alphabet to a binary code follows in precisely the same manner as described above for the four symbols representing genomic polymorphisms. Pattern discovery in this binary code follows as before.

Continuous-Valued Data

Continuous-valued data is different than either binary or categorical data in that there is an inherent order relationship among possible values of a feature since the features are numbers. Non-continuous numerical data, such as integers or whole numbers, can be considered as continuous-valued date, because they have an order relationship. There are many ways to cast continuous-valued (or numerical) data into the binary form useful for pattern discovery. A simple method is to first quantize numerical values into "binned" values. For example, with values ranging from 0 to 100, 0-33 can be quantized into a bin called "small;" values 34-66 into a bin called "medium;" and values 67-100 into a bin called "large." Thus, the continuous-valued attributes have been cast as categorical attributes.

The process as related to pattern discovery is described in detail elsewhere herein, wherein the categorical attribute has three values: (small/medium/large). A more sophisticated method that results in a sparser representation is to first decorrelate the continuous-valued instance (or signal). Decorrelation reduces the continuity of contiguous values in a signal, and therefore, information in the signal is compressed into a smaller set of features that effectively represent the original data. The decorrelated features may then be quantized and converted to a categorical representation. Transformations that decorrelate signals are well known to those skilled in the relevant art. By way of a non-limiting example, the wavelet transform described herein with respect to mass spectrometry proteomic data is one such embodiment.

Continuous-valued data useful in the present invention is the same as described elsewhere herein, except that each feature may be described by a continuous-valued number. The number of samples in an instance is the number of discretely sampled features. Each feature is an amplitude that may take on a continuous range of values. Such data are generally referred to as discrete signals. By way of a non-limiting example, with mass spectrometry data, each mass to charge ratio value (M/Z) has a corresponding amplitude represented by a real-valued number.

In one aspect, continuity of values for the features allows them to be re-cast in a categorical form. Such encoding may be done in the original representation of the signals or in any other continuous-valued transformed representation of the signal such as the wavelet transform, Fourier transform, or cosine transform, among others. Other continuous-valued transformed representations will be apparent to the skilled artisan when armed with the present disclosure. Once the continuous-valued signal has be transformed to a categorical representation, it can be represented in binary form as described elsewhere herein. Pattern discovery in this binary code follows as described elsewhere herein.

By way of another non-limiting example, a specific type of transformation and encoding for continuous valued spectrometry spectra representing two categories of data such as "cancer" and "normal" is described in the following example. The example is presented in "pseudo-code" format, wherein "{ }" demarcates blocks of operations that may be repeated over a set of cases. For example, the block of operations in braces following "foreach spectrum" is used to process each mass spectrum in the set of mass spectra. Other symbols, such as "if" and "else," denote logical operations where the block of operations in the braces is conditionally used depending on the result of a test of some condition, such as "coefficient is in mask Y of Normal." This pseudo-code representation of an algorithm will be familiar to the skilled artisan.

```
foreach spectruml {
    Resample onto uniform (m/z)^(1/2) grid;
    Compute the Discrete Wavelet Transform;
    Sort the coefficients in descending order;
    Create mask X, consisting of the top x% of coefficients;
    Create mask Y, consisting of the top y% of coefficients;
}
foreach Cancer spectrum {
    foreach Normal spectrum {
        if coefficient is in X mask of Cancer {
        if coefficient is in Y mask of Normal {
            discard the coefficient location;
        }
        else {
            retain the coefficient location;
        }
        }
    }
}
foreach Normal spectrum {
    foreach Cancer spectrum {
        if coefficient is in X mask of Normal {
        if coefficient is in Y mask of Cancer {
            discard the coefficient location;
        }
        else {
            retain the coefficient location;
        }
        }
    }
}
```

The resulting coefficient locations are merged together to form a global mask. The result of this process is the selection of the x % strongest discrete wavelet transform (DWT) coefficients from a spectrum in one category (e.g, "Cancer"), and then eliminating those that correspond to the same components in the strongest y % of any instance in the opposite category ("Normal" in this example). Increasing the x threshold tends to decrease the number of coefficients, and increasing the y threshold tends to increase the number of coefficients.

This embodiment of the invention utilizes known information about classes of data in order to replace the less common binary features (eg. "1's") with the more common binary features (eg. "0's). Here, if a feature is "set" (eg. represented by "1"), in an instance representing "cancer" and is set in any of the instances representing "normal," that feature may be ignored, since it will not participate in patterns that are exclusive to the cancer data. This method can be relaxed from requiring no occurrences in any normal instance, to possibly occurring some small number of times in the set of normal instances. Additionally, this method of making the data more sparse can be used for any type of data (binary, categorical, or numerical) if there is information that distinguishes amongst the instances comprising the data on which pattern discovery is conducted.

Categorical Encoding

Once the global coefficient mask has been constructed, encoding consists of determining the sign of each corresponding coefficient. In one embodiment of the invention, an ordinal number is assigned to each coefficient on the interval $\{1, L\}$, where L is the number of features. A binary fingerprint is then constructed of a length 2 L, as follows:

$$b_i = \begin{cases} 1, & c_i > 0 \\ 0, & \text{otherwise} \end{cases}\Bigg]_{i=1}^{L} \text{ and } b_j = \begin{cases} 1, & c_i < 0 \\ 0, & \text{otherwise} \end{cases}\Bigg]_{i=1}^{L}$$

where $$j = i + L$$

where the $c_i$ are the Discrete Wavelet Transform coefficients, and the $b_i$ ($b_j$) are the bits in the fingerprint. That is, the first L bits in the fingerprint represent positive coefficients, and the next L bits represent the negative coefficients. In one aspect of the invention, this is the simplest form of categorical encoding which is more elaborate than binary. There are three categories; namely, positive, negative or zero. However, the general method of categorical encoding for binary pattern discovery according to the present invention is appropriately illustrated. By way of a non-limiting example, given "n" non-null (non-zero) categories, the binary fingerprint will be L·n bits wide. By way of another non-limiting example, there are 2 categories (positive, negative) in addition to the null, or zero category.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1

Pattern Discovery in Genetic Sequence Data

Recognizable patterns of genetic polymorphisms are referred to as "haplotypes". The concept of a "haplotype block", in which the SNPs within the block take on a small number of the possible permutations, can be used to understand the relationships between SNPs with a certain locale. For example, it has been shown in some cases that, though there may be thousands of theoretically possible SNP permutations within a block, only a handful are actually observed. This has to do with the molecular mechanisms underlying genetic variation. The reduction of features describing a population to a set of haplotype blocks is a practical advantage in that it reduces the overall dimensionality of the problem. As set forth herein for the first time, whether dealing with individual SNPs or haplotype blocks as features, the present invention offers significant advantages over the prior art of analysis of genetic polymorphism.

The data set forth in this example demonstrates, for the first time, the use of pattern discovery to find haplotype blocks in the human genome. These results, based on pattern discovery technology of the present invention as set forth in detail elsewhere herein, in the context of genomic variation (SNP) data, validate the known genomic property that diversity of genetic polymorphisms tends to travel in haplotype blocks. Existing methods of haplotype block detection rely on pairwise marker linkage disequilibrium measurements within a population. The novelty of the method shown here lies in its ability to directly detect associations amongst arbitrary numbers of markers simultaneously, rather than inference of multilocus disequilibrium from pairwise measurements. For this study, example data were obtained from Gabriel, et al. (2002, Science 296:2225-2229). This work, conducted at the Whitehead Institute, set the stage for the Human HapMap project, a follow-on to the SNP Consortium's dbSNP project. Gabriel et. al. demonstrated that the genome can be objectively parsed into blocks of limited diversity punctuated by spans of significant recombinational diversity. The methodology used was based on analysis of pairwise marker linkage disequilibrium (LD), but required extensive statistical conditioning of the data prior to LD calculations. Gabriel et al. studied the distribution of haplotype block sizes derived from four populations, 30 parent-offspring trios (90 individuals) from Nigeria (Yoruba), 93 members of 12 multigenerational pedigrees of European ancestry, 42 unrelated individuals of Japanese and Chinese origin, and 50 unrelated African Americans. Their results show that the average haplotype block size is significantly larger in the European and Asian populations as compared with the Yoruban and African American populations.

The present invention involves computing patterns of SNPs, and then looking for allele frequencies among patterns that occur in a relatively large percentage of the population, referred to herein as "high support patterns." In part, patterns in the present invention represent marker linkages in a specific subpopulation. Thus, if there exist blocks in which limited marker diversity exists, these blocks should appear in a histogram as a contiguous grouping of markers that tend to occur with high frequency in the high-support patterns.

Figure 19:
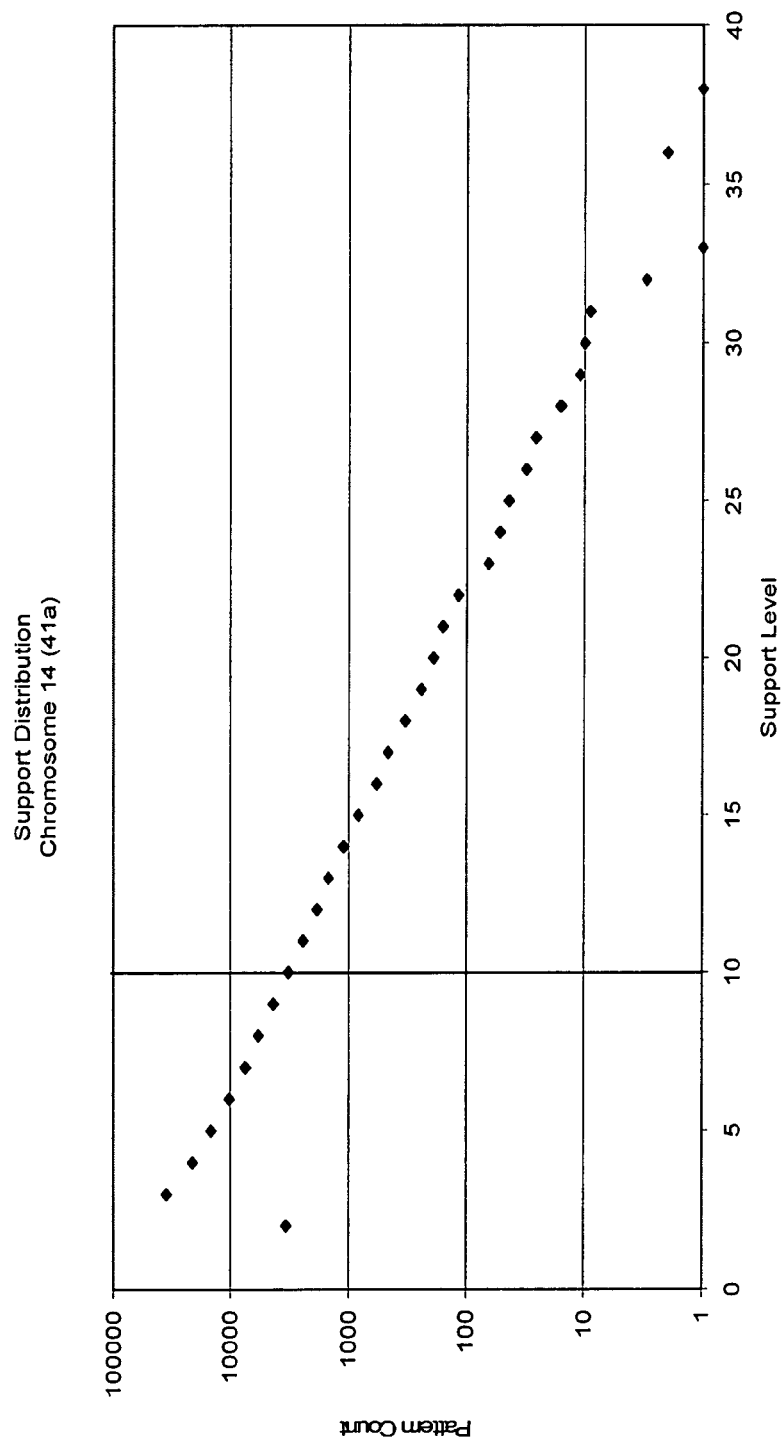
FIG. 19 is a graph illustrating the support distribution of patterns discovered among European chromosomes up to initial support level of 3.
Figure 20:
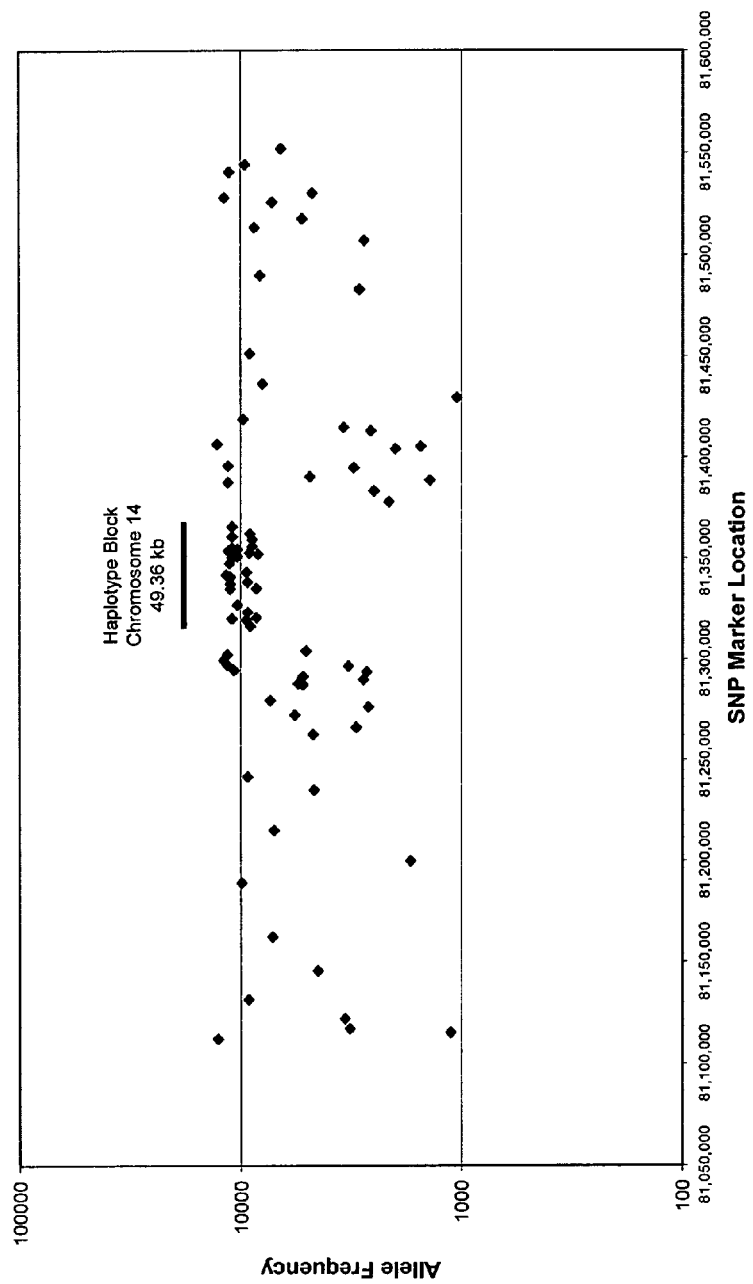
FIG. 20 is a graph illustrating marker frequency in high-support patterns. Patterns with support greater than or equal to 10 were selected (13,245 patterns from the European population). The logarithm of the number of times a marker occurs in such patterns is plotted versus the chromosomal location of the marker (ubiquitous markers are omitted from the graph for clarity). A haplotype block of approximately 50 kb in length is shown centered at chromosomal location 81,341,000.

As a test, the largest population, "population A" (corresponding to the European population) was selected for analysis in the present invention. Within this population was selected the largest contiguous grouping of marker data, corresponding to chromosome 14. Data for one chromosome 14 pair of was arbitrarily chosen for each of the 93 individuals described above. These data were then formatted into a form suitable for categorical pattern discovery. A total of 115,032 patterns were discovered up to an initial support level of 3 (the support of a pattern is the number of individuals in which that pattern is found to occur). These patterns were then re-matched to the input data to discover their actual support, shown in FIG. 19. A support level of 10 was arbitrarily chosen to limit noise inherent in low-frequency allelic associations. The total computation time required to discover the patterns was, for example, 21 seconds on a 2.0 GHz Pentium 4 processor with 1 GByte RAM, running the Linux operating system. The resulting pool of patterns was examined to determine the frequency with which each marker occurs. It was observed that in the raw data, the corresponding "marker frequency" was exactly 1, since, by definition, every marker appears once in each chromosome. FIG. 20 shows the distribution of marker frequencies in high-support patterns.

Patterns of SNPs were identified, as described herein for the first time, to delineate haplotype blocks. In pattern discovery terms, this translates to spatially dense, high support patterns. As shown in FIG. 20, a block of markers that frequently occur among high-support patterns is clearly seen as a relatively uniform and high-frequency block imbedded in a much more variable distribution of markers with a much lower average frequency of occurrence. The size of this block, 49.36 kb, is consistent with the distribution of haplotype block sizes shown in Gabriel, et al. (2002, Science 296:2225-2229). Significantly, this result is based on simultaneous linkages of arbitrary numbers of SNPs, compared with the prior art, in which other investigators were able to account only for pairwise correlations, using LD.

Figure 21:
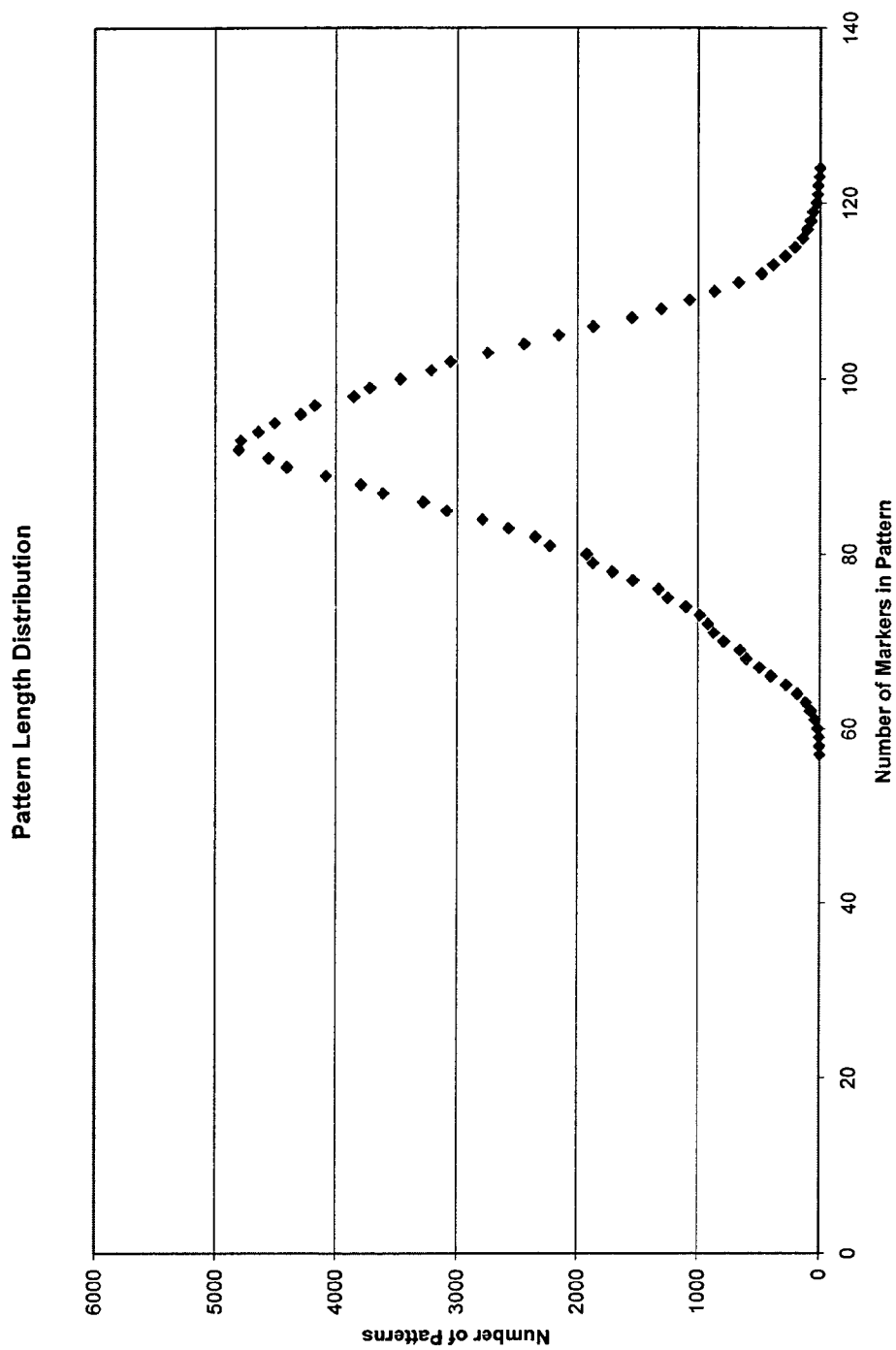
FIG. 21 is a graph illustrating the distribution of the number of SNP markers in patterns. The mean number of SNPs per pattern is 91.6, while the minimum is 57 and the maximum is 124 out of a total of 124 markers in the data.
Figure 22:
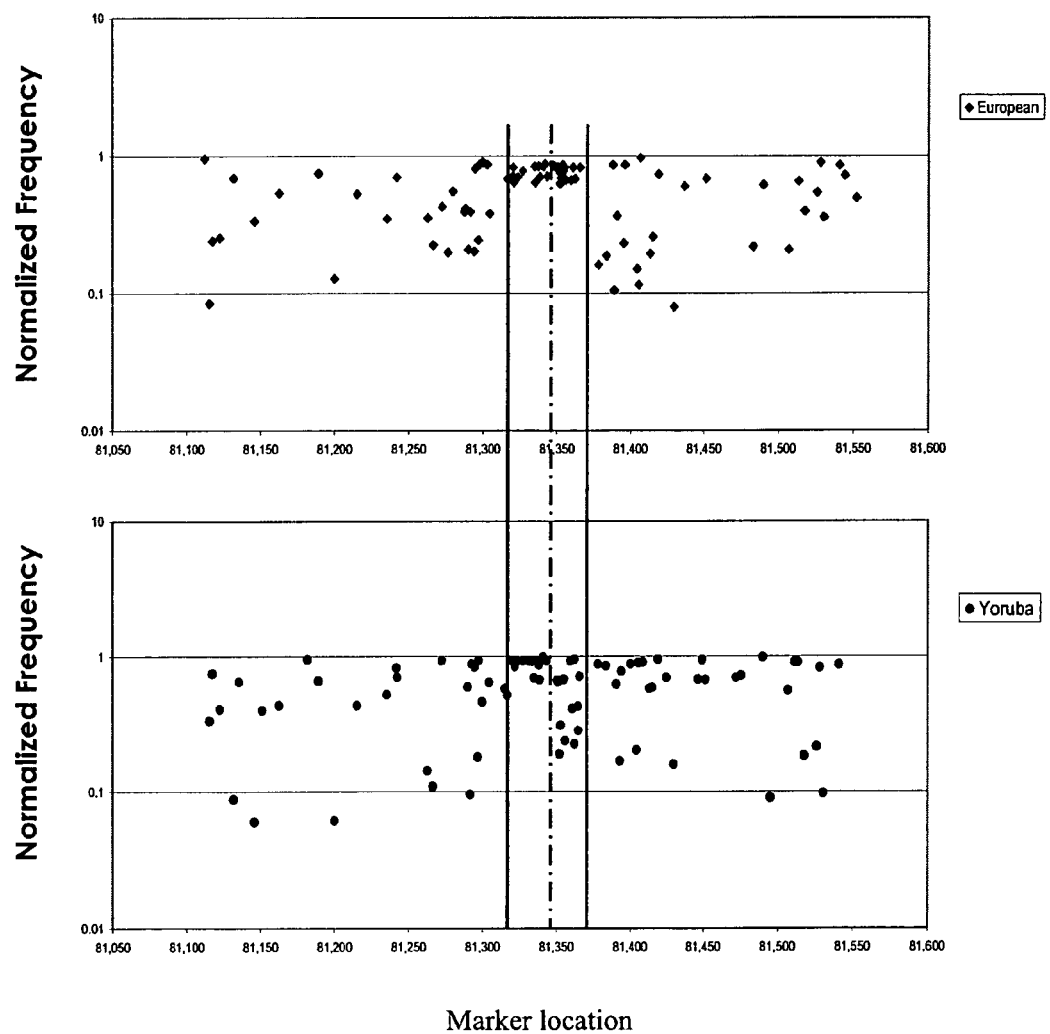
FIG. 22 is a graph illustrating a comparison of the haplotype block structure in chromosome 14 for European and Yoruban populations.

Gabriel et. al. showed that the Yoruban population has haplotype blocks of significantly smaller size, and concluded that the European (and Asian) populations have undergone an evolutionary bottleneck more recently, and thus the haplotype blocks have not been eroded by recombination to the same extent as the African populations. FIGS. 21 and 22 show clear evidence for this effect in the haplotype block in Chromosome 14. The graph in FIG. 21 is a pattern-based marker frequency distribution for the European population. The graph in FIG. 22 is the corresponding graph for the Yoruban population. The blocks indeed correspond to each other, but the Yoruban block is about half the size. This size difference is again consistent with the results of Gabriel et. al. Interestingly, recombinational erosion seems to have taken place preferentially from the right-hand end of the block.

The present invention therefore demonstrates, for the first time, that the pattern discovery methods set forth herein operate on genomic SNP data, and can recover characteristics of genomic variation, namely that the diversity of genetic polymorphisms tends to travel in haplotype blocks. Further, pattern discovery can accomplish this in a statistically unbiased and computationally efficient way In this example, a portion of the data available in the Gabriel study was analyzed, and it has now become apparent that it is computationally straightforward to extend this result to the entire genome.

Example 2

Pattern Discovery in Proteomic Mass Spectrometry Data

Medical diagnosis depends on the association of quantitative biological measurements with disease. The definition of what constitutes a valid biomarker is broad, encompassing any biological measurement that is indicative of physiological state. Such states may include genetic variations (genetics), gene expression (genomics), proteins or peptide fragments found in bodily fluids or tissue (proteomics), and concentrations of metabolites in cells (metabolomics). Examples of protein biomarkers used for cancer diagnosis are prostate-specific antigen (PSA) for prostate caner and CA-125 for ovarian cancer. However, a problem with single protein biomarkers such as those described above is low sensitivity and specificity. For example, 33% of patients with high PSA levels have benign disease, while PSA measurements within normal ranges may miss up to 65% of prostate cancers. Further, CA-125 is typically not observed at elevated levels until ovarian cancer has reached stage III, which stage has a poor prognosis for the patient. Recently, there has been great interest in utilizing multiple protein biomarker analysis for improved prediction of disease (Petricoin, et. al., 2002, Lancet 359:572-577).

Application of Pattern Discovery Methods to Ovarian Cancer Data

While pattern discovery can be used with any type of biomarker measured by any method, the example presented herein for the first time concerns protein biomarkers from mass spectrometry (MS) data. Specifically, data made available by the U.S. Food and Drug Administration/National Cancer Institute Clinical Proteomics Program Databank for ovarian cancer (website: <<ncifdaproteomics.com/ppatterns.php>>), was analyzed. This particular application of the present invention demonstrates validation of the experimental method, in contrast to those methods in the prior art previously used to study this data.

The methodology of the present invention comprises (a) decomposing the original MS data into a collection of features, (b) selectively removing noise features, (c) encoding the remaining features into categories, (d) performing categorical pattern discovery on this data representation, and (e) selecting patterns whose presence indicates healthy/diseased status.

The data consisted of 216 mass spectra; 95 from healthy individuals ("normals") and 121 from subjects with stage I, II, or III ovarian cancer ("cancers"). The disease stages associated with the cancer spectra were not provided with the data. The spectra posted on the NCI web-site were culled from an original sample size of 248 on the basis of a quality measurement as explained in Conrads et al. (2004, Endocrine-Related Cancer 11: 163-178). Even so, the present invention identified what appeared to be variations in the quality of spectra based on background noise levels and features of the data that seem to correlate with the sample ID number.

After downloading the dataset, ¼ of the data were immediately set aside for validation studies. Importantly, the validation data remained unobserved until all work was completed on the pattern discovery methods ultimately used for classification. Such practice avoids a common error in evaluating the ability of a method to generalize by "training" a method to a particular data set. The remaining ¾ of the data were termed "training/testing" data, since a portion of these data were used to train models of the invention and a portion were used to test the models of the present invention.

The pattern discovery algorithm set forth herein for the first time works on a categorical description of data. Because the SELDI MS data consist of continuous-valued signals, it is necessary to first encode the data in a categorical form before running pattern discovery. Four different methods were evaluated, as will be described below: wavelet-based encoding with cumulative binning of values, direct M/Z encoding with cumulative binning of values, cross-correlation encoding with cumulative binning of values, and direct M/Z encoding, selection of significant M/Z values, differential binning of values.

The data as obtained from the NCI/FDA web site consisted of a set of ASCII files for each case. Each file had approximately 300,000 M/Z values and corresponding ion current amplitudes. The M/Z step size in these files had increments that increased approximately as the square root of M/Z, however, the step size, in sqrt(M/Z) increments, was not constant. Accordingly, the first step in processing the data was to interpolate original data to a uniform sampling in sqrt(M/Z). The interpolated data set had 262,144 samples, with uniform sqrt (M/Z) step size, and M/Z units ranging from 700 to 12,000.

Wavelet-Based Encoding with Cumulative Binning of Values

The wavelet transform is a signal processing method that represents signals at multiple resolutions. The low resolution portion describes slowly varying features in the data while the higher resolutions describe sharp transitions. Mathematically, this transformation provides optimal localization in both the time and frequency domain. In the present example, the "time" independent variable is replaced by M/Z. Additionally, the wavelet transform tends to decorrelate features in a signal providing a more compact representation. The motivation for using wavelet-based encoding for this data is that the signals consist of a slowly varying background component punctuated by occasional sharp peaks representing high concentrations of ions at specific M/Z values. Additionally, it is observed that peak widths vary across the spectrum, making it difficult to model at a single resolution.

The specific steps followed to obtain the wavelet-based encoding with cumulative binning are as follows. First, data was downsampled by a factor of 8. This was done using a polyphase filter function in MATLAB (The Mathworks, Inc., Natick, MA) which includes anti-aliasing and as flat a frequency response as possible in the passband. This processing reduced the signals to 32,768 samples. Next, the discrete wavelet transform was preformed using MATLAB functions in WAVELAB (Donoho et al., Stanford University, website: <<www-stat.stanford.edu/~wavelab/>>; Stanford, Calif.). In this step, signals were decomposed into scale and frequency components. The number of wavelet transform coefficients was equal to the number of samples in the original signal, however, most of the information in the signal was concentrated in a relatively small fraction of the transform coefficients. For example, a reasonably good approximation to the signal could be reconstructed from the largest magnitude 10% of the coefficients.

Next, a fingerprint was constructed from significant wavelet transform coefficients. Wavelet transform coefficients were sorted in decreasing magnitude, then wavelet transform coefficients were binned into several amplitude bands based on their percentile. The subsequent ranking procedure was conducted by selecting coefficients whose magnitude was in the upper tenth percentile, followed by recordation of the locations of these coefficients, separately for positive and negative coefficients to preserve the sign of coefficient. Then, coefficients were selected whose magnitude was in the upper 15 percentile. Again, locations of the coefficients were recorded, including previously selected coefficients. The ranking procedure was continued in 5 percentile steps, up to 95%.

Bits for each magnitude threshold and sign were stored in the fingerprint. These were encoded by adding an offset to the numbers for each set. For example, bits 0- 32,767 were used to encode information about the first magnitude threshold for positive wavelet transform coefficients, 32,768-65,535 were used for the first magnitude threshold, negative signs, 65,636-131,071 were used for the positive, second magnitude threshold bits, and so on. Thus, the maximum bit-width for the fingerprint was 2×(number of thresholds)×(length of resampled signal).

The procedure described herein has the advantage of allowing small peaks to match into larger peaks. This is necessary, since it was observed that the peaks in normal or cancer instances occurred at the same locations but did not always have the same magnitudes, even when spectra were normalized. However, there is an issue in that the. To avoid the potential problem that distinguishing features for cancer versus normals may be the relative size of peaks, as well as absence or presence of peaks, training data for known classes was used to eliminate wavelet transform coefficients in the fingerprint that do not convey unique information about their class. This was done by looking at each potential wavelet transform coefficient, as selected above in magnitude thresholds, and determining whether any of the opposite class instances have corresponding wavelet transform coefficients that pass the same magnitude and sign test as well. If such an instance existed, then that wavelet transform coefficient was not included in the fingerprint.

This process as described herein provides the required sensitivity to distinguish both large peak differences and small peak differences. For example, a cancer instance may have a peak at some scale in the wavelet domain that is only in the 10 percentile category, but if none of the normal instances has a peak at that location and scale above this threshold, that "bit" is saved in the fingerprint. For large peaks, it may be that a normal instance has a peak greater than 95% of other samples, again, at a specific scale. However such a "bit" may be excluded because one or more training set cancer instances also has a peak at that location and scale.

By using 18 amplitude thresholds from 10% to 95% in steps of 5%, and setting the threshold for in-case equal to that of out-of-case, 192,594 bits were generated for the fingerprint file of 162 test/train data. The average number of bits for all instances was 1,189 bits. The average number of bits for the 71 normal instances was 634, while the average for the 91 cancer instances was 1,622. This indicates that the cancer instances are more "unique" than the normal instances and explains why the classification of cancer is more robust than normal. Pattern discovery of the present invention performed on the entire 162 set of data yielded 395,753 patterns. The highest support pattern obtained was 53.

It was also determined that when the in-case and out-of-case thresholds are equal, or when the out-of-case threshold is less than in-case threshold, the bits are "pure" and therefore, all patterns are pure. These parameters can be relaxed, such as in the case where such relaxation may be required for robustness, by setting the out-of-case threshold larger than the in-case threshold, allowing "mixed" bits and potentially mixed patterns.

Direct M/Z Encoding with Cumulative Binning

Direct encoding creates a categorical description of the data using amplitudes at each M/Z sample. This method provides a more natural representation for interpreting patterns as specific sets of M/Z values, and would be preferable for data that could be accurately classified based on a few discrete peaks. As descried herein, the information in the SELDI MS data used in this study was distributed, and thus, direct encoding did not work as well. The method used for direct encoding with cumulative binning is identical to the wavelet transform method described above, except that the transform step is left out.

Direct M/Z Encoding, Selection of Significant M/Z Samples, and Differential Binning Direct M/Z encoding, selection of significant M/Z samples, and differential binning directly encodes amplitude values using a statistical test to select informative M/Z samples. Unlike the other methods, it uses differential binning, setting a single bit corresponding to a given amplitude bin.

For this method, the M/Z samples from mass spectra in the training data were processed using a non-parameteric, statistical test (Wilcoxon Mann-Whitney) to determine which samples were significant in differentiating between the two classes of instances. This reduced the number of features that had to be encoded prior to running pattern discovery. In this particular aspect of the method used, a bit was defined as a "set" if the amplitude at a selected M/Z value fell within a particular range of values. This step corresponded to quantization of the amplitude values using a set of amplitude thresholds to define a set of quantized bins.

Cross-Correlation Encoding with Cumulative Binning

Cross-correlation of signals with an accurate reference model is a sensitive method for finding peaks. The motivation for this method is that the result should be less sensitive to normalization of the signals. For the reference signals, we used averages of the training data for cancer and normal cases. Since the classification of test or validation data is blind to its class, cross-correlations were taken to both cancer averages and training averages and the difference signal encoded.

Example 3

Statistical Method for Comparison to Pattern Discovery

In order to compare pattern discovery results to conventional statistical techniques, a method was developed utilizing Fisher's two-class linear discriminant analysis to classify spectra. This algorithm identifies the best hyper-plane that separates two classes of data. A critical part of this method involves inverting a matrix related to the covariance. This was done using Singular Valued Decomposition. Hence, this method is referred to herein as LD/SVD. This technique does not specifically utilize localized information in the spectra, but rather, it forms weighted linear combinations of all M/Z values.

Classification Results

Several careful computational studies were conducted on this data. The first study involved repeated random draws (~100) from the above-described training/testing set using a portion for developing a pattern-based empirical model and the remainder as a blinded test set to evaluate the model. The combined result from this series of random draws provides an estimate of the classification accuracy expected on a novel set of similar data. A second set of experiments used a "leave-one-out" approach. In this approach, all of the training data, except for one, were used to develop a model. The multiple random draws and the "leave-one-out" experiments were conducted with both the linear discriminant and the wavelet transform methods. This model was used to predict the class of the remaining, left out, instance. In experiments where both methods were used, the results were very similar.

Many variations of data transformations and parameters were examined, including various resampling rates, high-pass filters, thresholds used in binning, and selection of bits by significance measures. Specific parameters varied depending on which of the four methods was used. At the end of the experiments, after methods and parameters were frozen, the validation data set was processed to provide a completely blinded evaluation of the prediction accuracy.

A summary of classification results is shown in Table 1. "LD/SVD" refers to the conventional statistical method (linear discriminant/singular valued decomposition) used for comparison to pattern discovery. "Wavelet" indicates wavelet-based encoding with cumulative binning. "Direct M/Z (C)" stands for the direct M/Z encoding method with cumulative binning. "Direct M/Z (D)" refers to direct M/Z encoding with differential binning and selection of significant bits based on a statistical test. "X-correlation" indicates the cross-correlation method. The last row, "Conrads, et al.," gives estimated classification accuracies and validation results based on the work illustrated by Conrads et al. (2004, Endocrine-Related Cancer 11:163-178). Although the results provided by Conrads et al. has been widely reported as "100% specific and sensitive," in fact, only 4 out of 108 of the models described by Conrads give such a result on the validation data described in that publication. More importantly, the 4 specific patterns are selected by performance based on the validation data itself. In Conrads, et al., distributions showing sensitivity and specificity for 58 of the 108 models are presented. In the present application, the estimates shown in Table 1 are based on these distributions using optimistic assumptions (for example that the remaining 50 models were eliminated without reference to the validation data).

TABLE 1

Summary of Data Classification Results

| Method | Classification accuracy (%) | | Results for validation data | |
| --- | --- | --- | --- | --- |
| | Cancer | Normal | False negatives | False positives |
| LD/SVD | 99 | 97 | 0 | 1 |
| Wavelet, present invention | 98 | 93 | 0 | 3 |
| Direct M/Z (C) | 91 | 89 | 2 | 3 |
| Direct M/Z (D) | 94 | 89 | — | — |
| X-correlation | — | — | 2 | 3 |
| Conrads, et al. (estimated) | 98 | 91 | 1 | 2 |

As shown in Table 1, the best classification result was obtained with the non-pattern based statistical method. The next best result was obtained using a wavelet-based pattern discovery method of the present invention which, although pattern based, also utilizes information that is distributed across many M/Z values through the wavelet transform. It should be emphasized that, although the methods in Table 1 can be ranked, there is actually very little difference between the results since the variation in performance corresponds to differences in classification of only a few instances.

The success of a simple statistical technique like LD/SVD has important implications concerning the nature of this data. This method is non-local, using information distributed across the full M/Z range, and therefore does not utilize biomarkers corresponding to specific M/Z values. Additionally, this method succeeded even when the data was subsampled below the-resolution of specific peaks. However, further evidence that non-local information carries important information for classifying the data is the success of the wavelet based pattern discovery method of the present invention. The technique of the present invention also utilizes information distributed throughout the spectra, since wavelets decompose a signal into multiple scales, including low-resolution components.

Analysis of Patterns

Although the LD/SVD approach resulted in the best classification accuracy, it does not provide any information concerning specific peaks (biomarkers) in the spectrum that help to distinguish cancers from normals. Therefore, an important part of the present invention is the analysis of discovered patterns. Because the methods disclosed in the present invention are complete and deterministic, and have the properties of finding all patterns among all combinations of cases, there are an enormous number of patterns. In order to concentrate on a few, a subset of the patterns was considered that successfully classified the data into normal and cancer categories. This concentration was selected, because it is known that such patterns identify significant, discriminating features.

To employ patterns of the present invention for classification of unknown instances, patterns are identified in the training case for each class of data. Patterns discovered in one class of data are matched into the data set of the opposite class. For example, patterns that are discovered in the "cancer" class are matched into the "normal" class. If these patterns match in the opposite class of the training set (also referred to as a "hit"), the patterns are filtered out, since they are not specific to the class of data in which they were discovered. Such patterns become probes for the test (or validation) data. The number of discovered patterns depends upon many factors, including the total number of cases and the specific encoding method, but generally, hundreds of thousands of probe patterns are obtained using the methods of the present invention.

Each pattern is associated with a specific subset of instances. The subsets overlap, and thus, many of the "bits" (representing features in the encoded space) are correlated between patterns. In order to classify unknown instances from test (or validation) data, the ensemble of probe patterns was used. A score for each unknown was calculated based on the number of probe patterns from each class that hit in the unknown case.

Tables 2 and 3 illustrate the numbers of patterns from the wavelet-based and direct M/Z encoding methods with cumulative binning. The first row illustrates the total number of probe patterns discovered in the training sets for cancer and normal data. Following the total number of probe patterns are the numbers of patterns that are "pure" with respect to the validation data. That is, none of the "pure" patterns hit in the opposite class of validation data (no false positives). These patterns correspond to 100% specific patterns in the sense of Conrads et al., where specificity has been evaluated by performance on the validation set.

However, the maximum support of these patterns, shown in the last row of Tables 2 and 3, is less than the total number of cases, so each pattern only classifies a subset of the data. To achieve 100% sensitivity, the present invention uses ensembles of patterns. There are many combinations of the probe patterns that together cover all cases. The third row in Tables 2 and 3 illustrates the minimum number of highest support patterns needed to achieve 100% sensitivity.

TABLE 2

Wavelet-based Pattern Discovery with Cumulative Binning

| Patterns | Cancer | Normal |
|---|---|---|
| Probe patterns from training data | 303,086 | 53,495 |
| Pure patterns that generalize to validation data | 163,493 | 30,196 |
| Minimum number of patterns to cover all cases | 12 | 10 |
| Maximum support/total cases | 54/121 | 45/95 |

TABLE 3

Direct M/Z Pattern Discovery with Cumulative Binning

| Patterns | Cancer | Normal |
|---|---|---|
| Probe patterns from training data | 388,256 | 29,320 |
| Pure patterns that generalize to validation data | 180,652 | 12,167 |
| Minimum number of patterns to cover all cases | 12 | 15 |
| Maximum support/total cases | 66/121 | 33/95 |

FIGS. 1 through 18 illustrate examples of patterns superimposed upon averaged signals for cancer and normal cases. FIGS. 1 to 9 illustrate patterns from the direct M/Z encoding with cumulative binning. FIGS. 10 to 18 illustrate patterns from the wavelet-transform method, remapped to the M/Z domain. In these figures, signals have been scaled to have zero mean and unit variance. The (red) curves show the average of cancer signals while the (green) curves show the average of normal signals. The (blue) pluses show the M/Z locations from a subset of the ensemble of pure, generalized cancer patterns described above. The selected patterns have a support of at least one eighth of the total number of instances (a total of 15 for the cancer cases).

Also illustrated in FIGS. 1-18 by (black) circles are the locations of the Petricoin patterns described by Conrads et al. (2004, Endocrine-Related Cancer 11: 163-178). It is important to emphasize that while the present invention used averaged signals to indicate peaks associated with patterns, pattern discovery uses the entire collection of cases. Also, it should be noted that not every peak in the average spectra is important. The reason that pattern discovery has picked out particular features is that these regions correspond to locations that differentiate normals from cancers.

There are many peaks in the mass spectrometry data disclosed herein, but most of them are not significant in that they do not differentiate between classes (i.e., cancer vs. normal). Pattern discovery according to the present invention, combined with the differential filtering as described in detail elsewhere herein, enables the determination of particular sets of peaks that are significant. Graphic representation of averaged spectra themselves are not used to find peaks, but rather, to illustrate the location of significant peaks that have been found through pattern discovery. The average spectra provide a context for viewing the peaks, since it would be difficult to simultaneously visualize all of the spectra from both classes of data.

Figure 2:
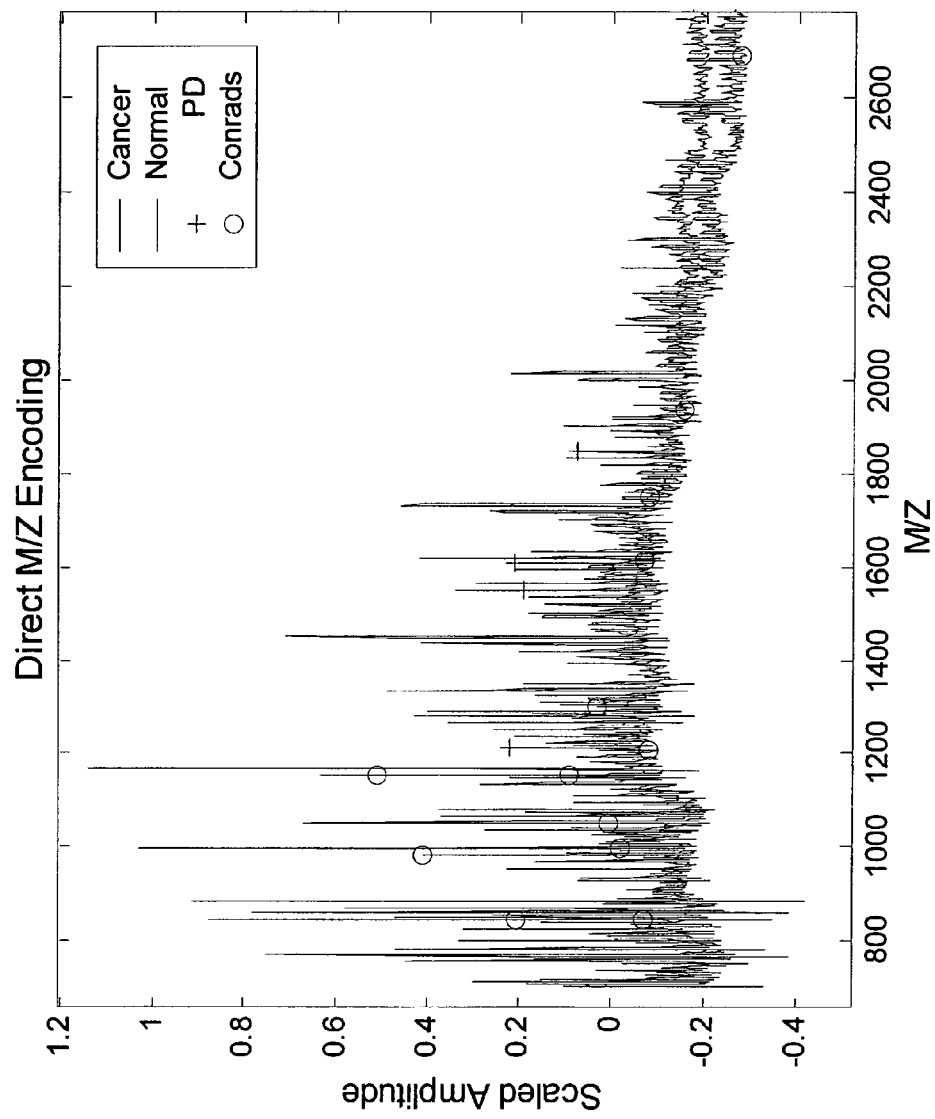
FIG. 2 is a graph illustrating a partially magnified view of FIG. 1.

FIG. 1 shows patterns from the direct encoding method for the entire M/Z range. Note that in FIG. 1, most of the larger peaks are not associated with patterns. In fact, many of the locations where pattern features accumulate (as seen by a high density of (blue) "+") have minor peaks that would not be distinguishable from background if they were not marked by patterns. FIGS. 2 through 9 display magnified regions so that individual features comprising the patterns can be seen. As with all pattern discovery methods, not every feature is meaningful. For example, in FIG. 2, illustrating an M/Z range from 700 to 2800, most of the features are probably not significant.

As validation of the methods of the present invention, it is noted that the M/Z range from 700 to 2800 in FIG. 2 also includes 12 of the features identified as significant by Conrads et al. Another significant feature is observed in FIG. 8, centered around an M/Z of 8602. There is a tight cluster of features from the patterns identified by the present invention, as well as some of the features identified by Conrads et al. This result indicates a significant biomarker discovered by both the methods of the present invention, and by Conrads et al.

Figure 3:
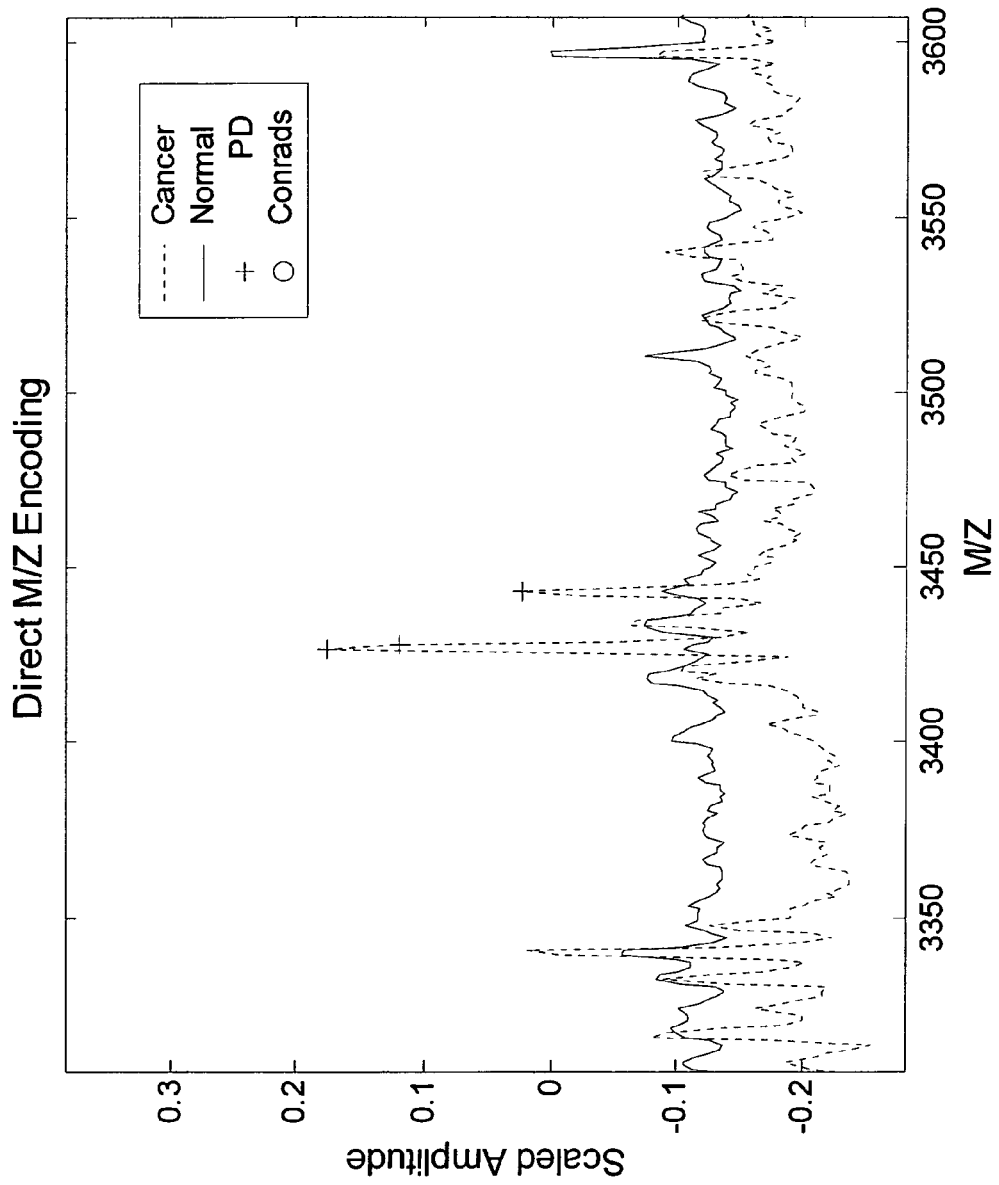
FIG. 3 is a graph illustrating a partially magnified view of FIG. 1.
Figure 4:
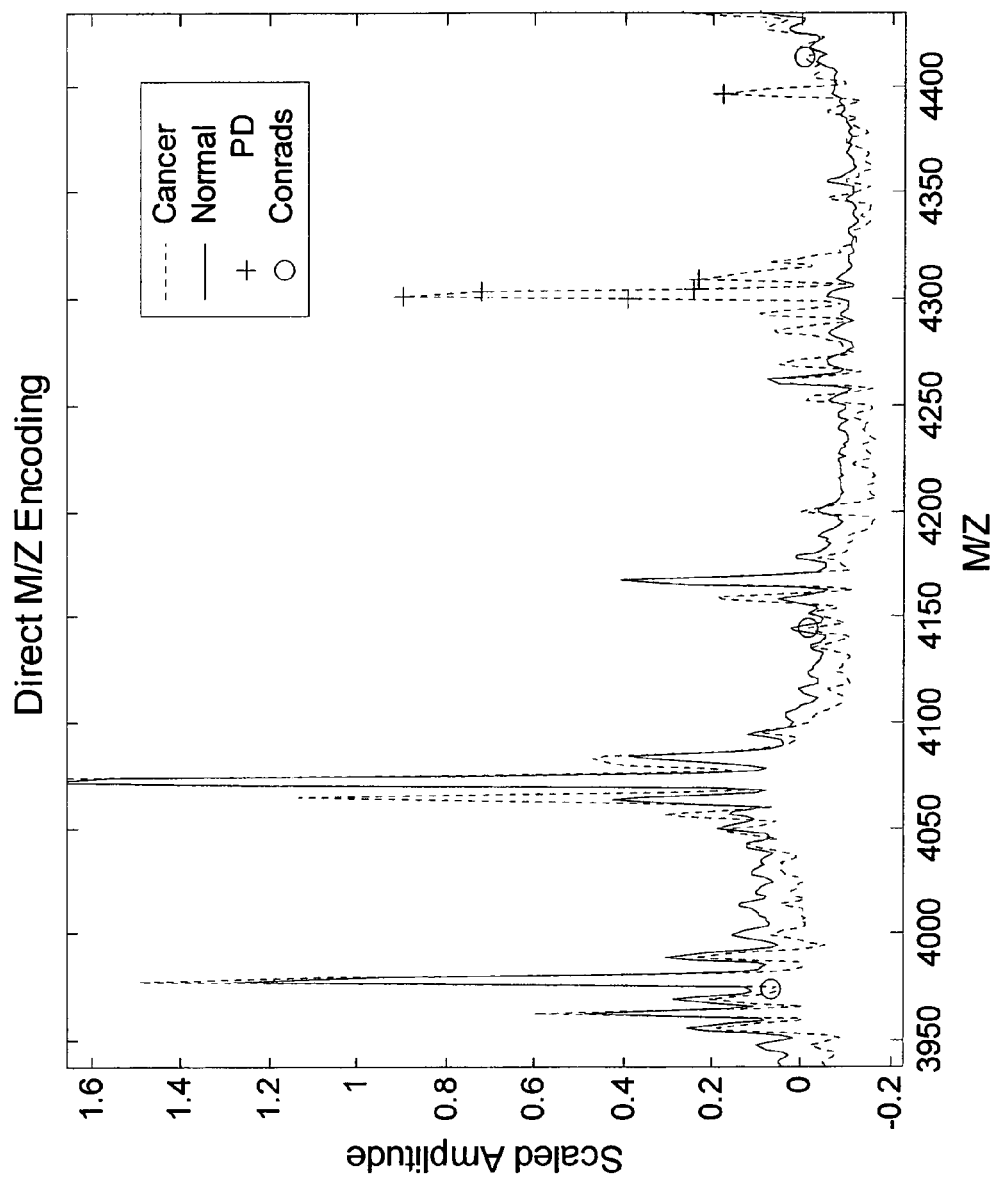
FIG. 4 is a graph illustrating a partially magnified view of FIG. 1.
Figure 5:
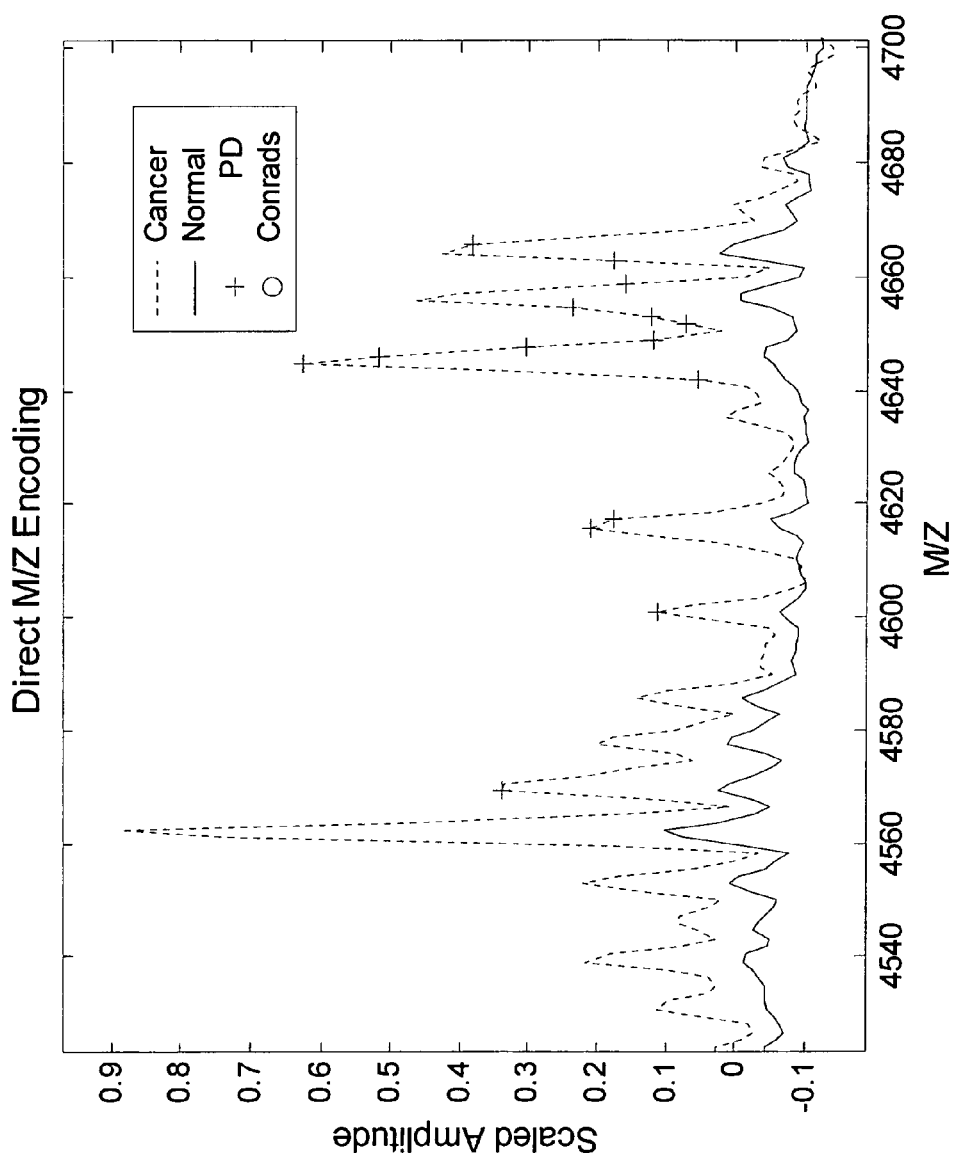
FIG. 5 is a graph illustrating a partially magnified view of FIG. 1.
Figure 6:
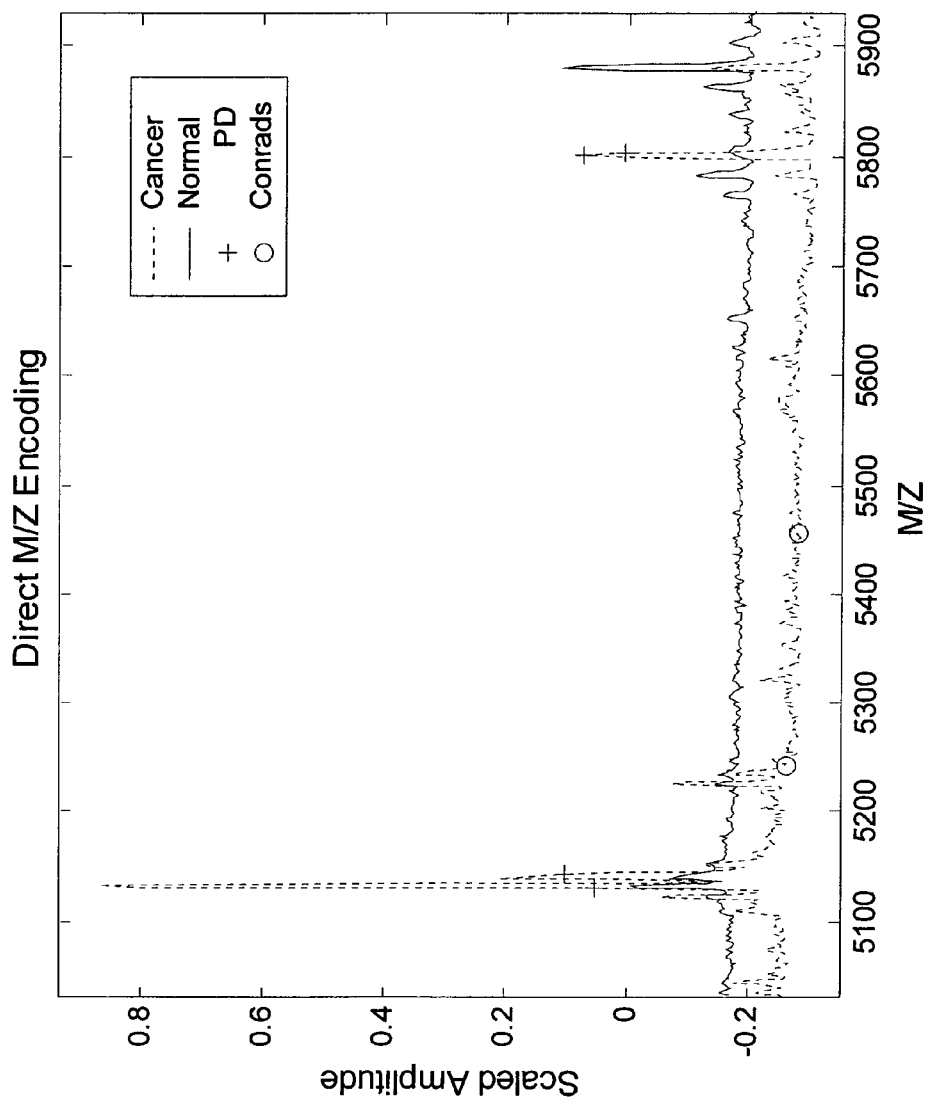
FIG. 6 is a graph illustrating a partially magnified view of FIG. 1.
Figure 7:
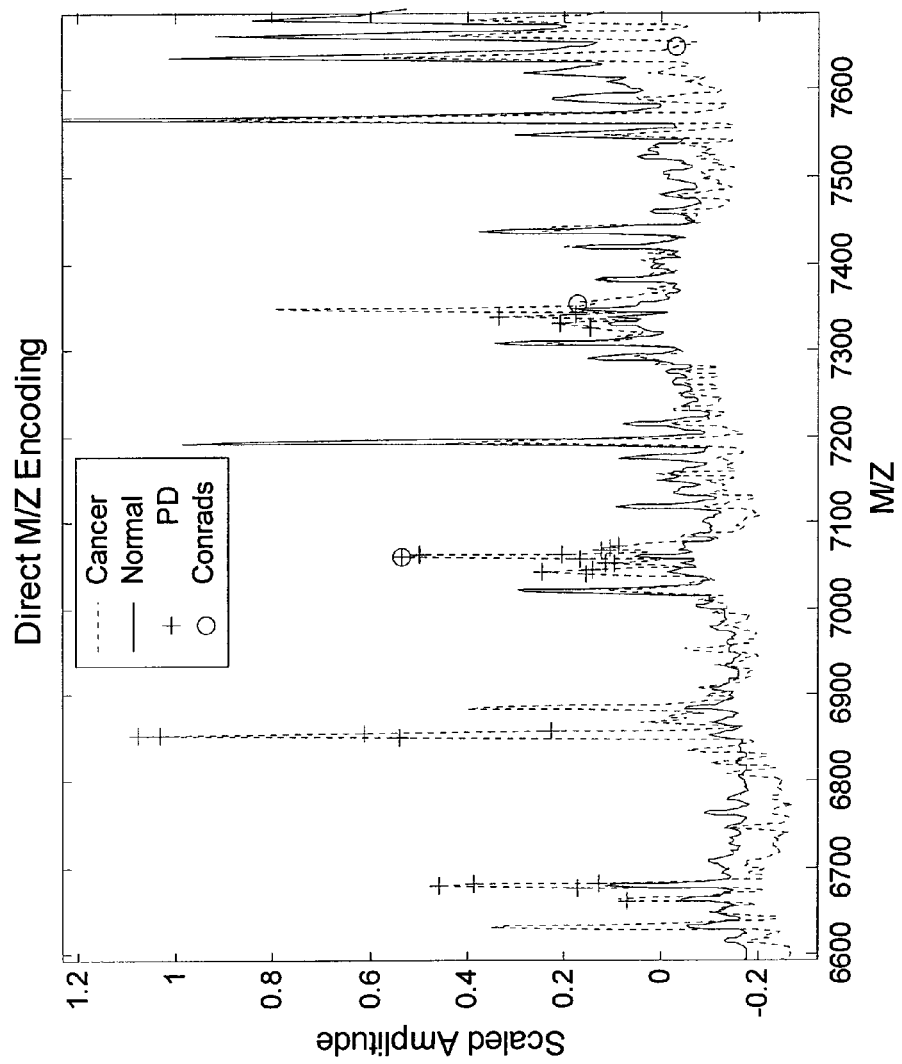
FIG. 7 is a graph illustrating a partially magnified view of FIG. 1.
Figure 8:
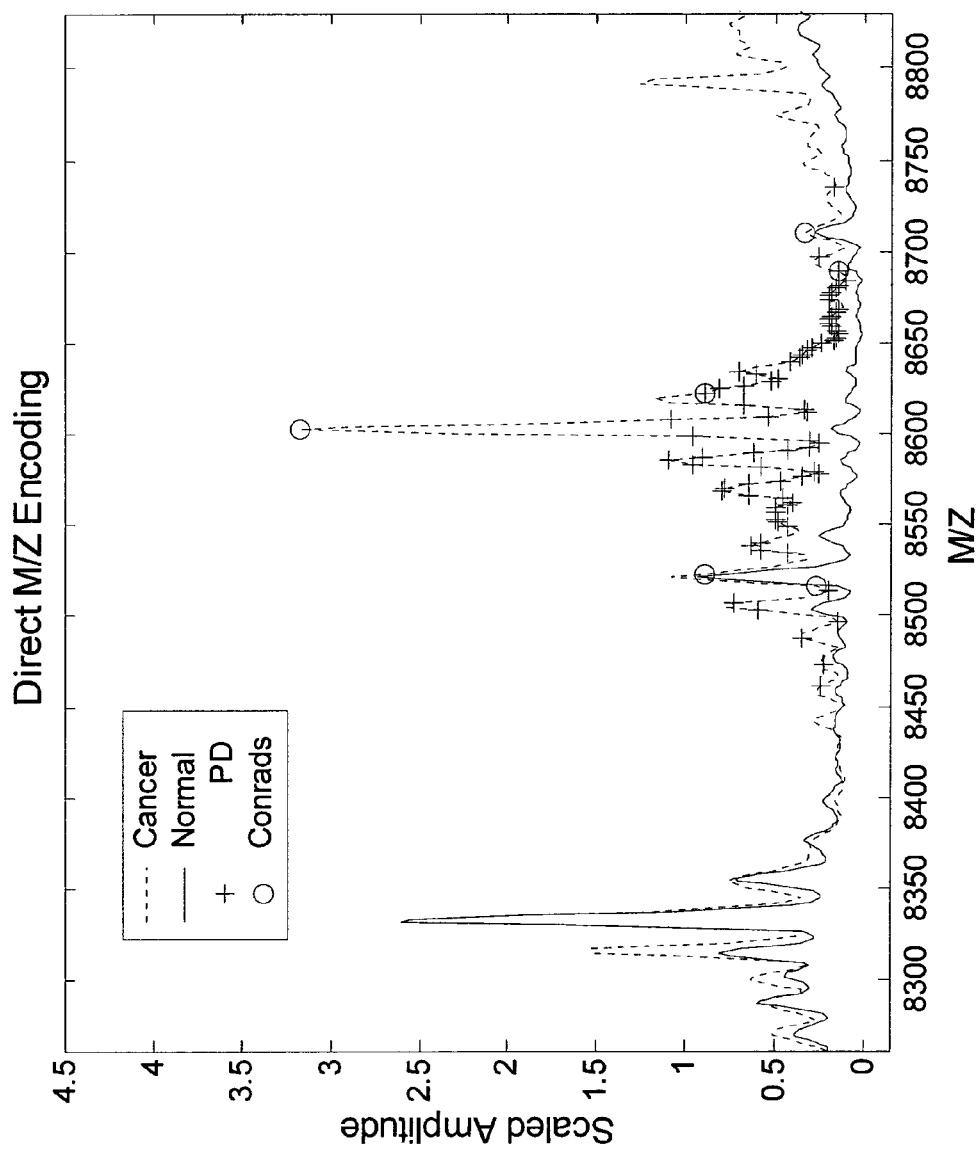
FIG. 8 is a graph illustrating a partially magnified view of FIG. 1.
Figure 9:
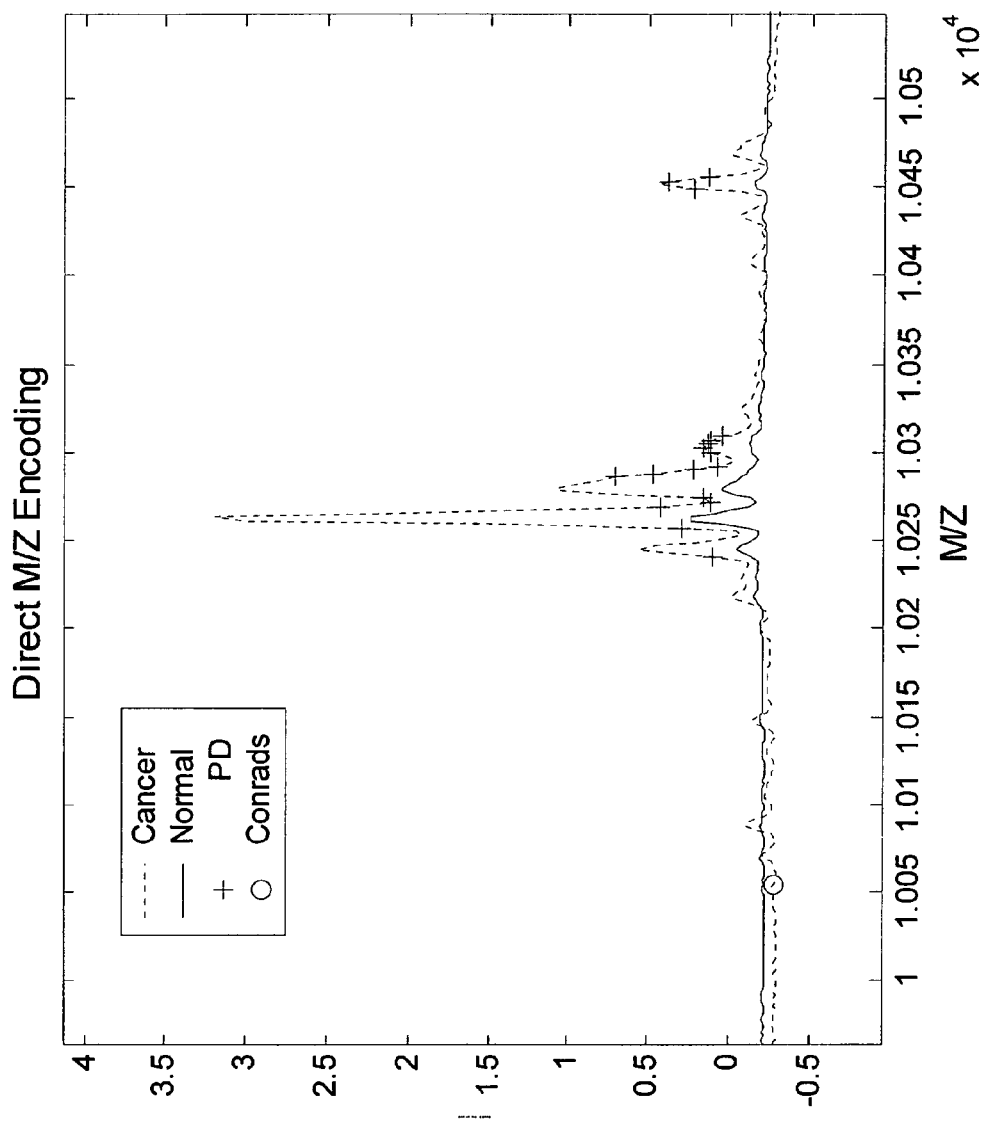
FIG. 9 is a graph illustrating a partially magnified view of FIG. 1.

Other significant regions within the Figures of the present invention include M/Z's between 3300 and 4700, as shown in FIGS. 3, 4, and 5. The feature centered at 4301 clearly distinguishes the average cancer from average normal signals. Others at 3425, 4397, 4600, 4618, and 4645-4667 are more subtle but occur at small peaks in the average cancer signal that are above a smoother background in the normal signals.

There are also three M/Z locations (3974, 4144, 4413) identified by Conrads et al. that appear to occur in regions that show no clear distinction between the cancer and normal signals. The region between 5000 and 5900, shown in FIG. 6, indicates two potentially distinguishing biomarkers around 5130-5145 and 5800. Again, there are two M/Z locations identified by Conrads at al. in this region, however the one at 5455 occurs at a location that is differentiated more by a base-line shift than an M/Z peak. Another region with many pattern features is M/Z from 6600 to 7400, shown in FIG. 7. The peaks at 6852 and 7060 look particularly significant. The peak at 7060 is also one of those found by Conrads et al.

However, the more significant peak at 6852 is only identified by a method of the present invention. Two other significant regions with peaks above background identified by pattern discovery methods of the present invention are located at M/Z's of 10260 and 10450, shown in FIG. 9. These findings show, for the first time, that critical biomarkers can be identified using methods described in detail herein.

Figure 10:
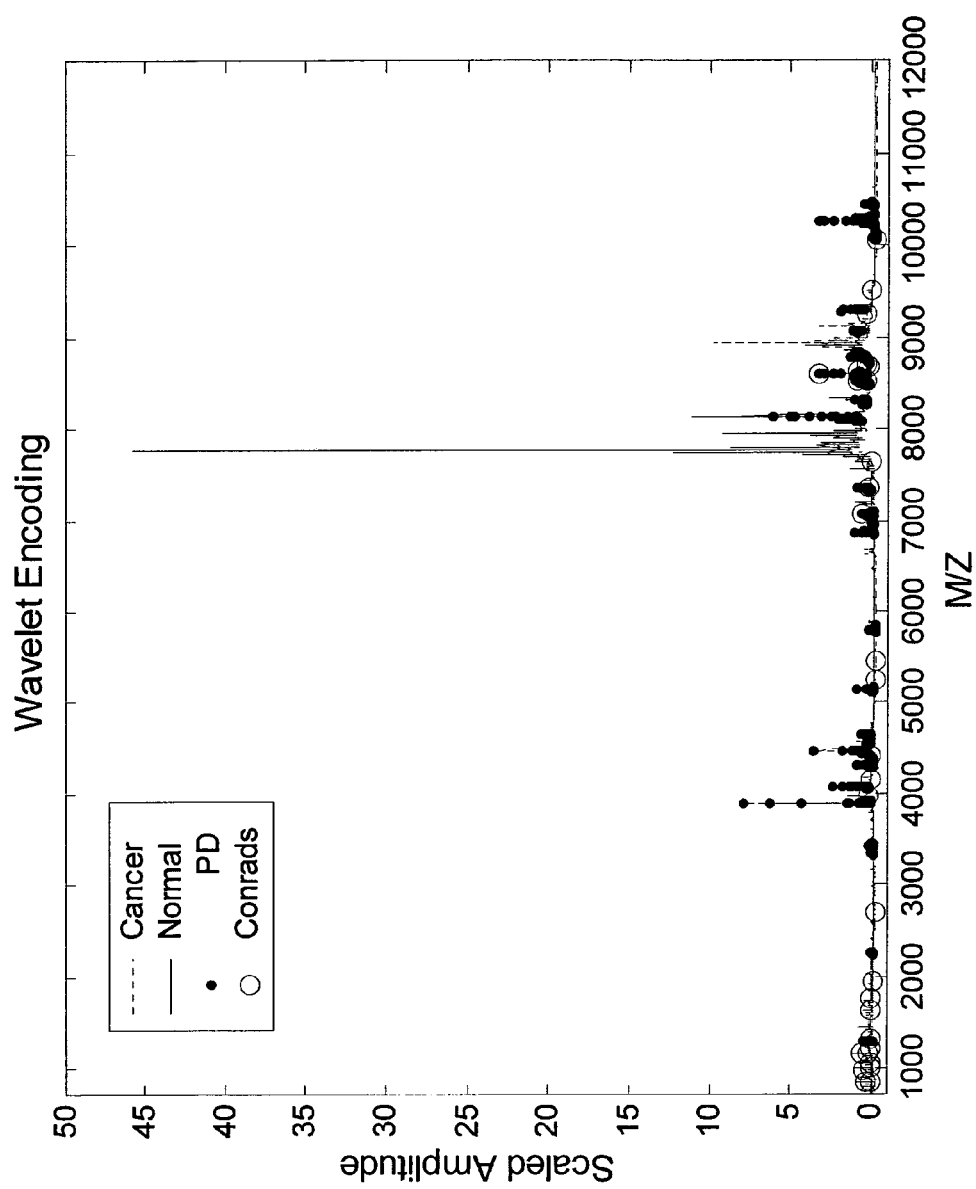
FIG. 10 is a graph illustrating discovered patterns obtained using the wavelet-transform method, remapped to the M/Z domain, for the entire M/Z range of mass spectrometric data. Patterns are superimposed upon averaged signals for cancer and normal cases. The X-axis represents the M/Z value of the data; the Y-axis represents the scaled amplitude of the data; dashed lines represent data from cancerous cells; solid lines represent data from normal cells; "plus" signs represent pattern discovery data obtained using methods of the present invention; circles represent data obtained by Conrads, et al. ((2004, Endocrine-Related Cancer 11:163-178).
Figure 11:
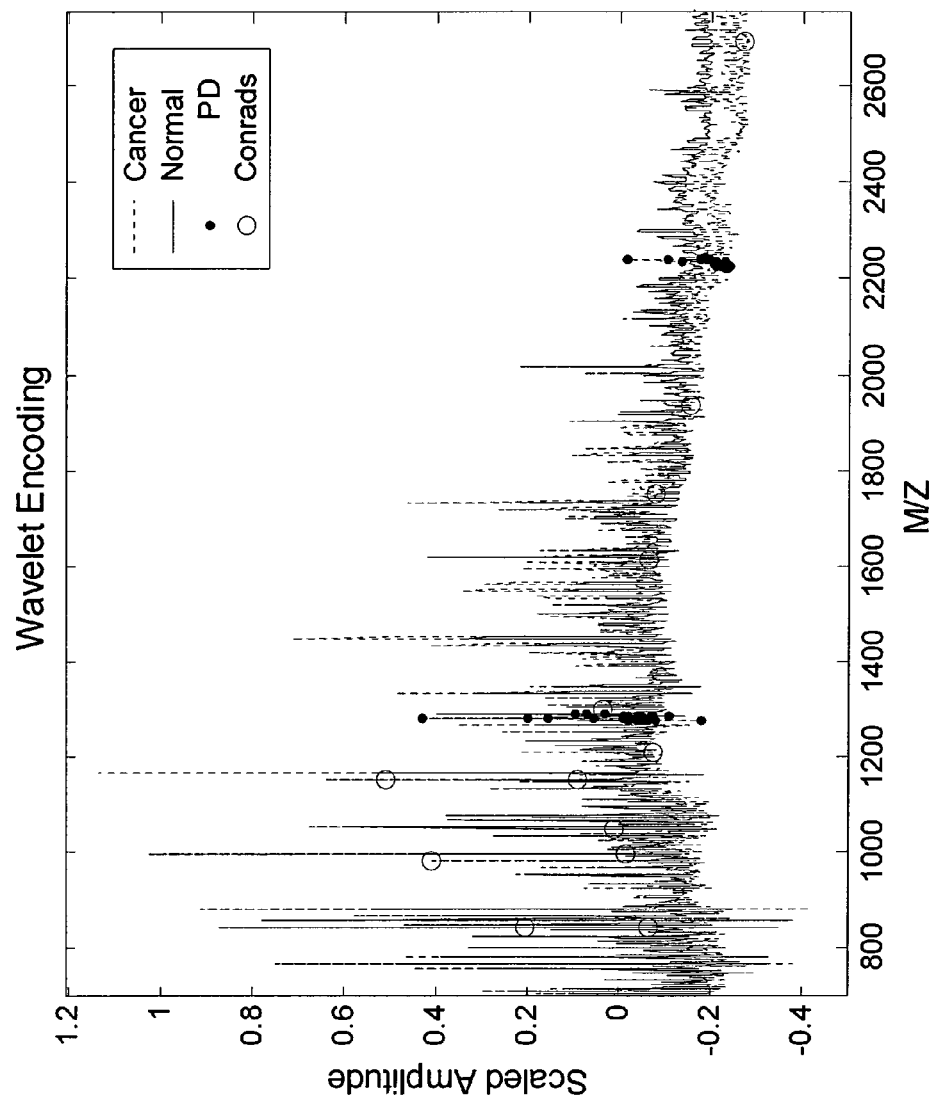
FIG. 11 is a graph illustrating a partially magnified view of FIG. 10.
Figure 12:
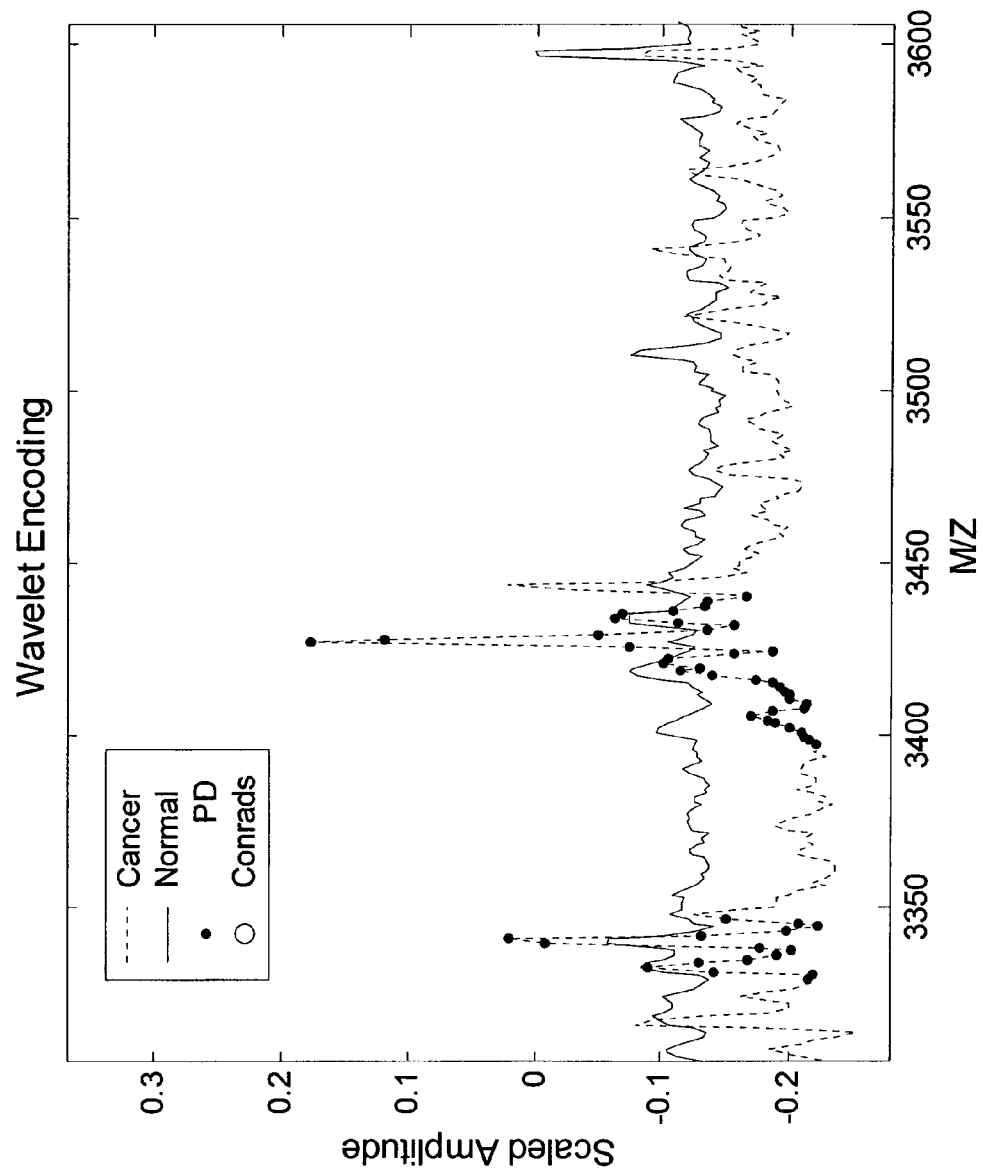
FIG. 12 is a graph illustrating a partially magnified view of FIG. 10.
Figure 13:
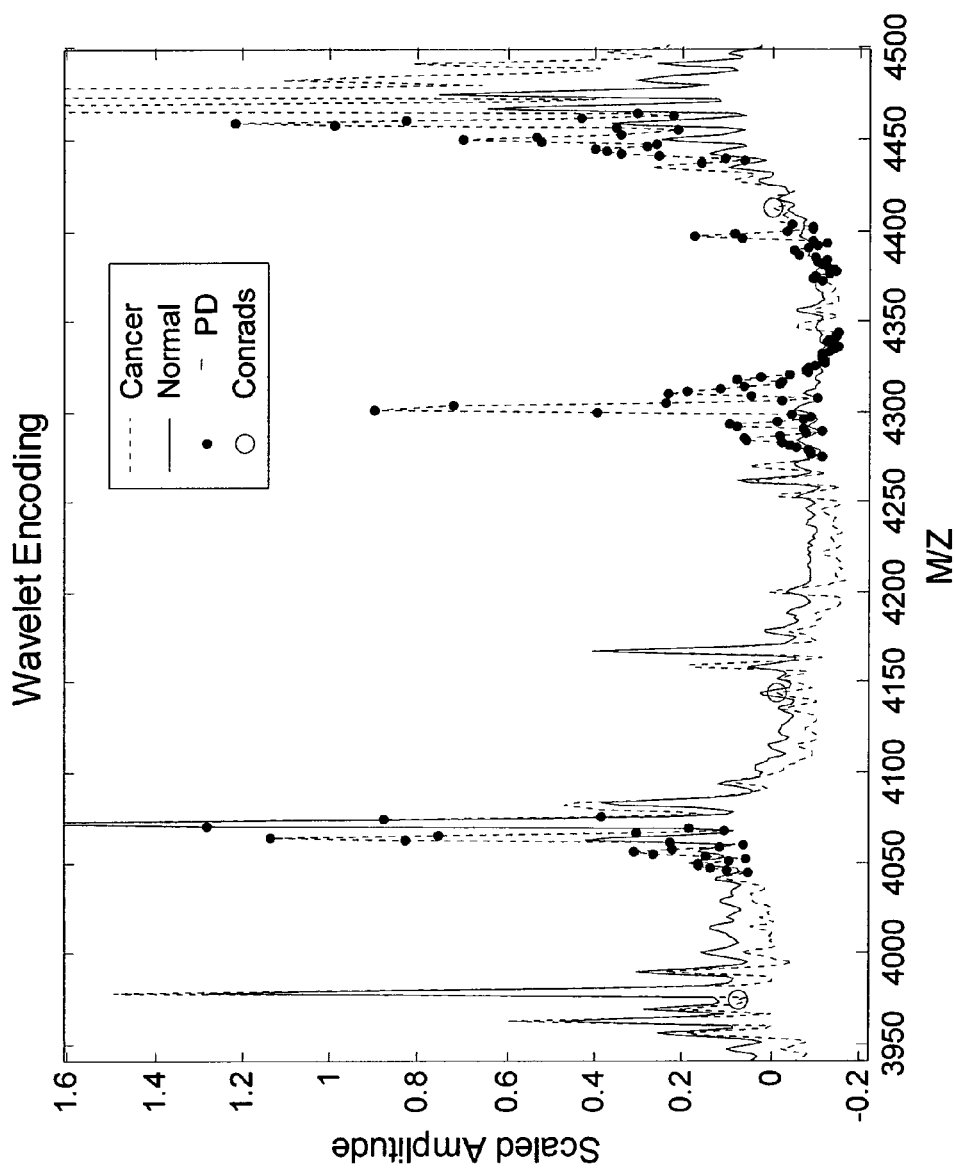
FIG. 13 is a graph illustrating a partially magnified view of FIG. 10.
Figure 14:
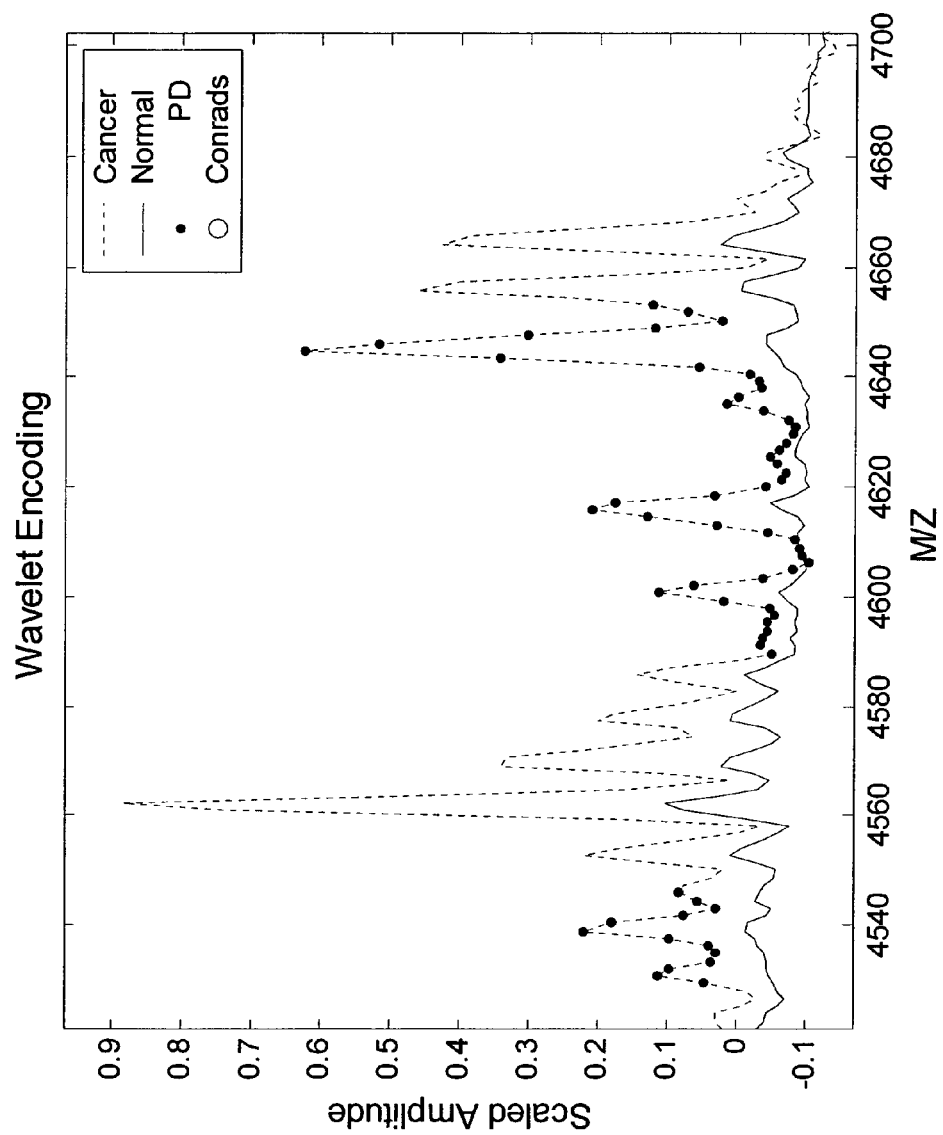
FIG. 14 is a graph illustrating a partially magnified view of FIG. 10.
Figure 15:
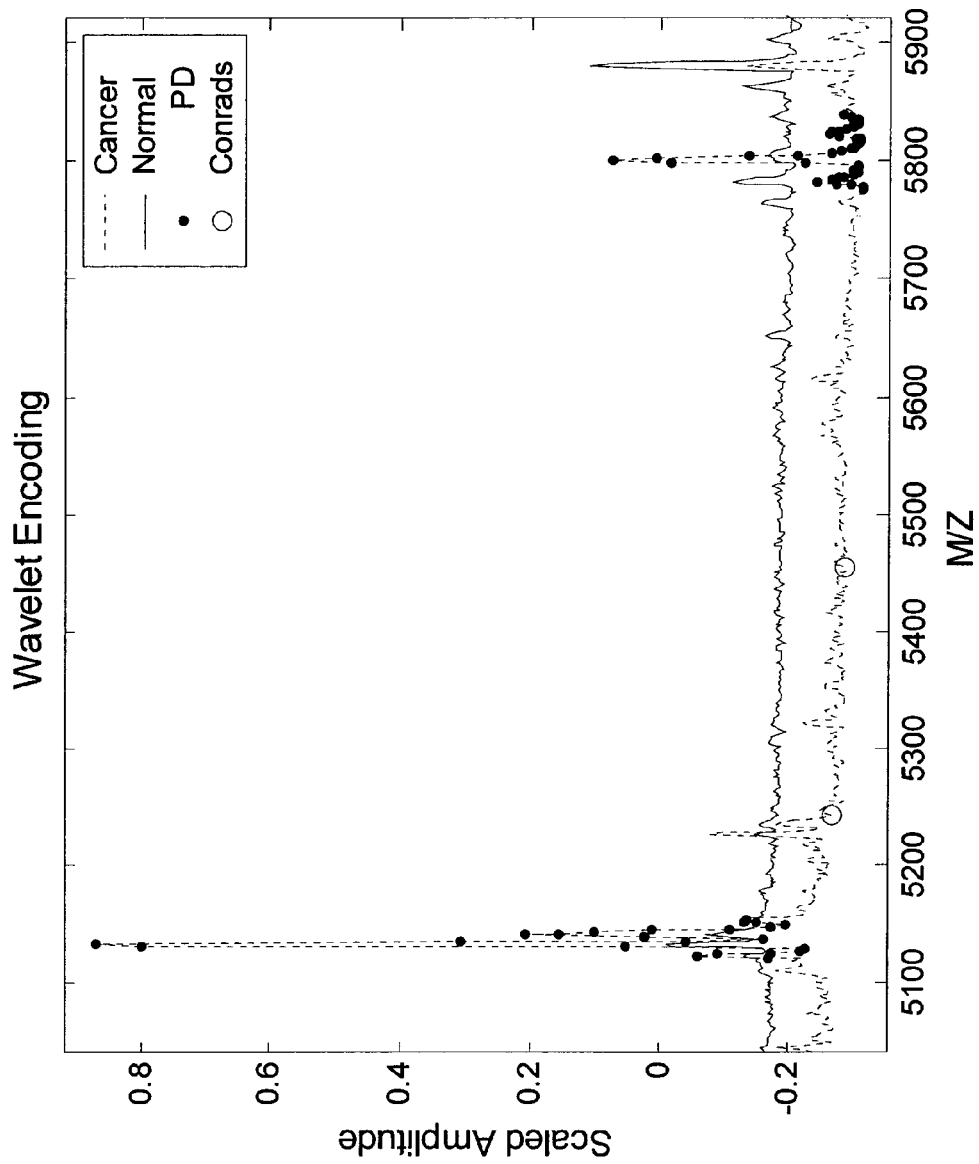
FIG. 15 is a graph illustrating a partially magnified view of FIG. 10.
Figure 16:
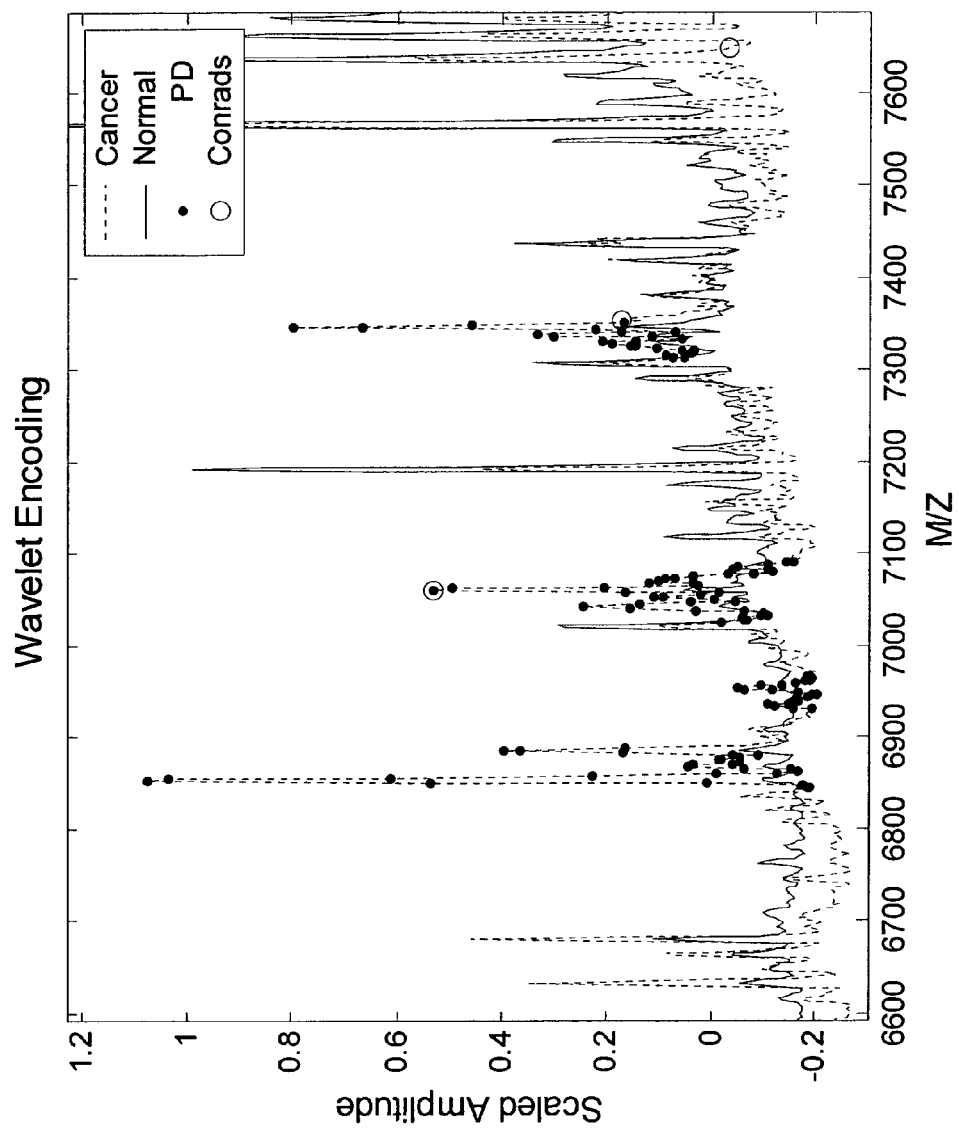
FIG. 16 is a graph illustrating a partially magnified view of FIG. 10.
Figure 17:
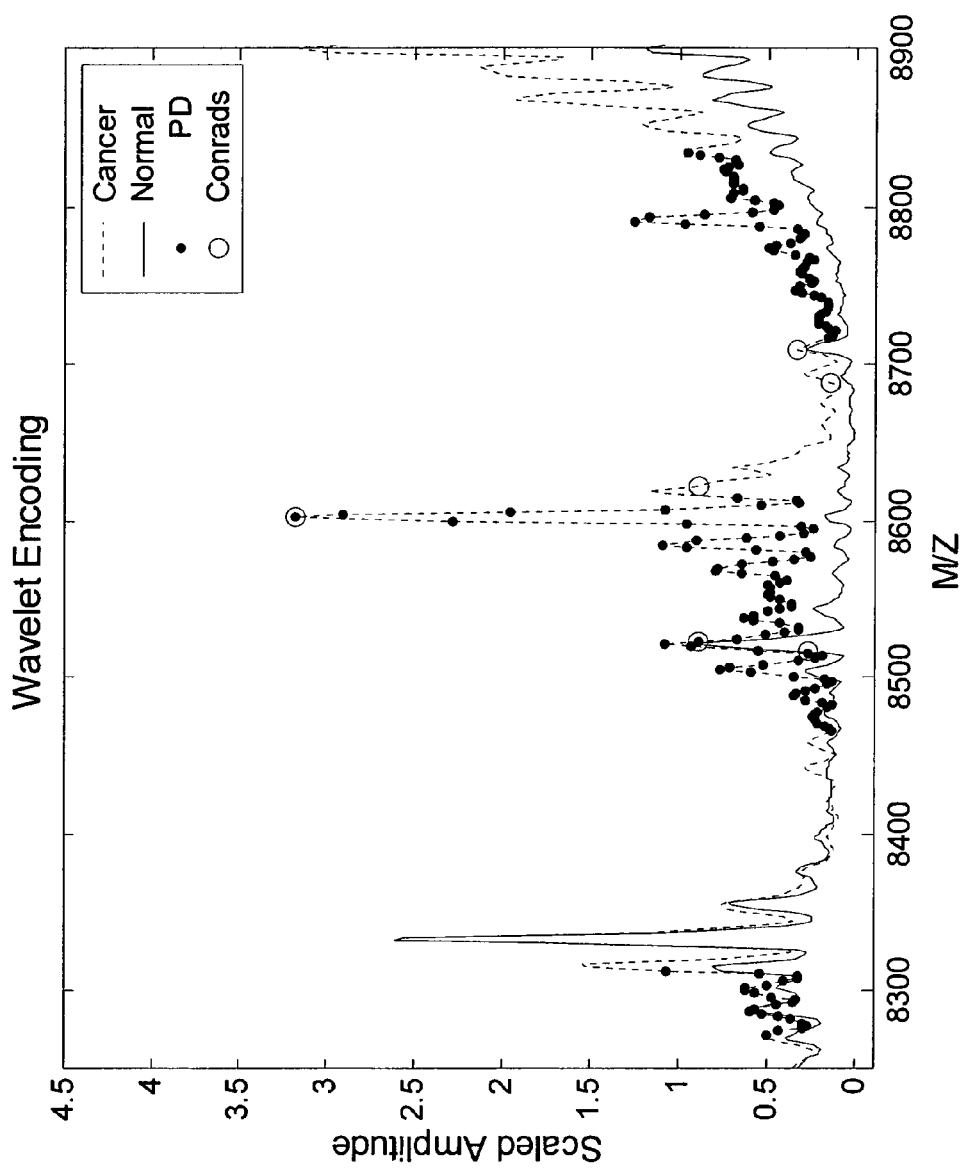
FIG. 17 is a graph illustrating a partially magnified view of FIG. 10.
Figure 18:
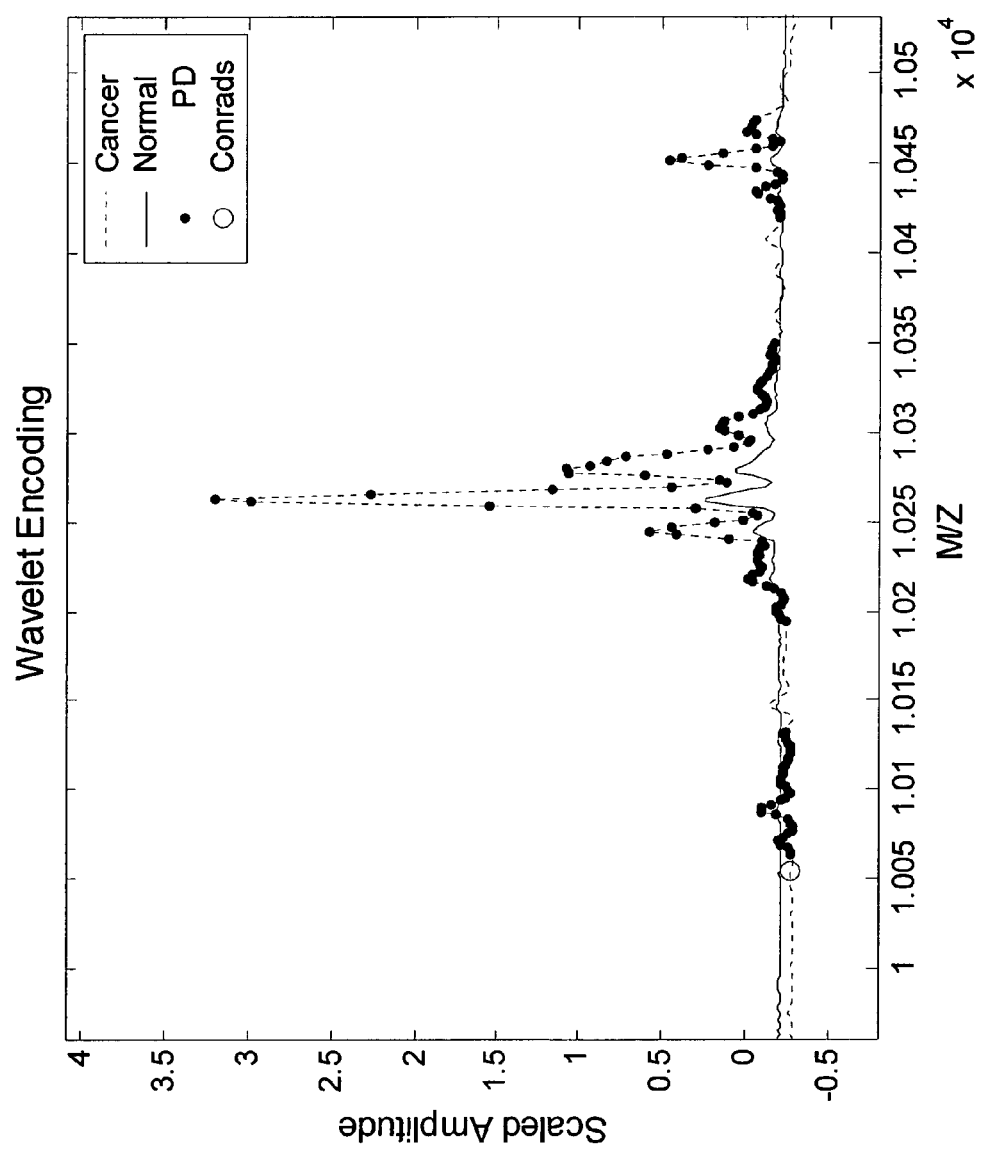
FIG. 18 is a graph illustrating a partially magnified view of FIG. 10.

FIG. 10 shows the full M/Z range for patterns discovered with the wavelet transform encoding of the present invention. Here, regions of wavelet coefficient patterns are marked by (blue) dots superimposed on the cancer signal. Again, the Petricoin patterns identified by Conrads et al. are marked by (black) circles. Because the wavelet method works in a domain that does not necessarily correspond to localized M/Z, these regions are distributed over a range of M/Z values. The extent of the M/Z coverage for a specific wavelet pattern is determined by the scale of the corresponding wavelet coefficient. As described elsewhere herein, the pattern features shown in these figures are those from patterns with support of at least 15 out of the 121 cancer instances. Also, to more clearly show localized features, patterns resulting from the lowest frequency wavelets have been filtered out. However, while these features are not shown in the figures, these features do play an important role in the classification results described above. The figures discussed herein show pattern features in most of the same regions as the previous set, however, broader contiguous regions are marked out because of the mapping of the wavelet transform coefficients to ranges of M/Z.

Comparison of Patterns Identified by the Present Invention with other Patterns

Correlogic Systems has developed an Ovarian Cancer diagnostic, OVACHECK (Bethesda, Md.), based on classification of MS spectra such as those used in the present invention. The Correlogic Systems software, PROTEOME QUEST, employs genetic algorithms and self-organizing maps to find patterns in data, and references the findings of Conrads et al. In comparing patterns obtained using the present invention to those obtained using Correlogic Systems' software, it is essential to understand the distinction between the two different approaches. Correlogic's diagnostic is based on an empirical model that classifies cases. The patterns identified thereby are the features upon which this classification is based.

While the patterns of the present invention also successfully classify this data, the present invention is further useful, and for the first time, to identify protein biomarkers that can be used to develop diagnostics. Although the NCI/FDA dataset utilized in the present invention cannot be used for this purpose, the patterns identified in the present invention clearly demonstrate how the present invention is useful for finding biomarkers represented by peak intensities in mass spectrometry data.

It should be noted that Conrads et al. (2004, Endocrine-Related Cancer 11:163-178) lists M/Z values for the 4 patterns identified therein that correctly classify a validation dataset. Each of the patterns comprises from 7 to 10 M/Z values. The classification of Conrads et al. is based on the Euclidean distance of unknown cases, using these specific M/Z locations to establish the dimensions of the space for this distance calculation. Thus, the patterns of Conrads et al. do not necessarily correspond to peaks in MS spectra. Rather, the patterns of Conrads et al. merely have to result in "good classification." In this sense, the technique used by Conrads et al. is similar to the Linear Discriminant method, except that Conrads et al only uses a portion of the data.

Alternatively, patterns identified by the present invention are useful to locate regions in the spectra that correspond to peaks resulting from protein fragments. Since the methods of the present invention are complete and deterministic, methods of the present invention are useful to identify many more patterns that cluster around peak features differentiating cancer from normal cases. The present invention can also be used to find many non-peak discriminating M/Z locations.

Classification of cases serves a guide to focus on informative peaks in the data. Examining locations of the Correlogic PROTEOME QUEST pattern features in the averaged spectra, it is found that such patterns identify the significant region of M/Z that distinguishes cancer cases from normal cases at and around 8600, as do patterns obtained using the methods of the present invention. Similarly, the Correlogic patterns also include features at or close to differentiating peaks identified by our patterns around 4400, 7060, and 7350. However, the rest of the Correlogic pattern features fall in areas that do not show any distinguishing peaks that might be associated with protein fragment biomarkers for cancer. Patterns discovered as part of the present invention, and selected using classification as a guide, include the same 4 peak regions. In contrast, however, the present invention has enabled, for the first time, identification of an additional set of ten differentiating biomarker regions around 3400, 4300, 4400, 4650, 5130, 5800, 6700, 6850, 10250, and 10450 M/Z.

Therefore, the present invention sets forth the detailed analysis of the ovarian cancer dataset from the NIH, NCI-FDA Clinical Proteomics Program using a novel method of pattern discovery. Data was classified with high accuracy using the patterns obtained as part of the invention, and using linear discriminants. The best results were achieved by methods of the present invention utilizing distributed information in the signals, rather than local features, showing that this dataset contains significant information regarding class that is not attributable to local biomarkers. Additionally, patterns discovered for the first time using the present invention were compared with those reported by Conrads, et al.. It was demonstrated herein for the first time that the methods of pattern discovery set forth herein provides unforeseen advantages for identifying significant biomarker peaks, finding over three times as many biomarkers that differentiate cancer from normal cases.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A program storage device readable by a machine, tangibly embodying a program of instructions executable by the machine to perform a method for finding patterns of genetic variability in genetic sequence data, said method comprised within:
   a) processing one or more polynucleotide sequences in the genetic sequence data, said sequences comprising a unique categorical representation for each of the unique bases comprising a polynucleotide, and eliminating representations in the sequences that do not vary across individuals, leaving only instances of variable representations, each of said instances of variable representations being described by a predefined set of attributes, each of the attributes having a unique category for each of the unique categorical representations;
   b) translating the categorical representation of each of said instances of variable representations to an equivalent binary representation by:
      i) assigning, for each attribute, a set of bits, the number of sets of bits equal to the number of categories that exists for the attribute, by means of a mapping function; and
      ii) combining the collection of said bits together into a single binary sequence for each instance;
   c) finding all binary patterns in said binary representation by:
      i) translating a set of instances of binary sequences comprising first and second binary values to a list of position indices of said first binary values, said position indices corresponding to the location of each of said first binary values within said binary sequences, wherein said second binary values are implicitly represented by the absence of an index corresponding to the position of each of said second binary values;
      ii) forming all unique subsets comprised of pairs of instances, corresponding to support k equal to 2, wherein k represents the number of instances in each unique subset;
      iii) finding patterns in the k=2 subsets, said patterns being the result of the application of the Boolean AND operator upon the instances in the subset, the result of which is a list of position indices common to the instances in the subset;
      iv) if more than one subset produces identical copies of a pattern, removing from further consideration all but one of said subsets, the canonical subset, which has produced a copy of the pattern;

v) if a null pattern occurs in a subset, removing said subset from further consideration;

vi) for each remaining k=2 subset of two instances, forming all possible k=3 subsets that can be formed by combining the remaining instances with the two instances in the k=2 subset without redundantly forming the same k=3 subset more than once;

vii) setting k=3 and repeating steps (c)(iii) through (c)(v) where k=3; and viii) repeating steps (c)(vi) and (c)(vii) for successively higher values of k until no more unique subsets of instances can be formed; wherein the resulting patterns correspond to the subset of maximum support k on which each of said resulting patterns has occurred;

d) translating said binary patterns back to a corresponding categorical representation by means of the inverse mapping functions of step (b)(ii).

2. The program storage device of claim 1, wherein method step (a) further provides that, when more than one of a particular binary value occurs within any group of bits, the possibility exists for ambiguity of more than one of any of a unique base being present at a particular corresponding location in a sequence of symbols.

3. The program storage device of claim 1, further wherein method step (a) provides for the substitution of a unique symbol for each of one or more entire haplotype blocks identified by said method, each of said unique symbols encoding a specific combination of genomic symbols within said haplotype blocks, and optionally wherein method step (a) further provides that the number of categories corresponding to one or more of said haplotype blocks can be a value selected from the group consisting of less than 4, equal to 4, or greater than 4.

4. The program storage device of claim 3, wherein each of said haplotype blocks comprises one or more genetic polymorphisms.

* * * * *